United States Patent [19]

Heidenreich et al.

[11] Patent Number: 4,897,419

[45] Date of Patent: Jan. 30, 1990

[54] PEST-COMBATING AGENTS BASED ON DERIVATIVES OF 2,3-DIAMINOMALEONITRILE

[75] Inventors: Holger Heidenreich, Kuden; Benedikt Becker, Mettmann, both of Fed. Rep. of Germany

[73] Assignee: Bayer Aktiengesellschaft, Leverkusen, Fed. Rep. of Germany

[21] Appl. No.: 211,798

[22] Filed: Jun. 27, 1988

[30] Foreign Application Priority Data

Jul. 17, 1987 [DE] Fed. Rep. of Germany ....... 3723621

[51] Int. Cl.$^4$ .................... A01N 37/34; C07C 121/66; C07C 121/70; C07C 121/78
[52] U.S. Cl. .................................. 514/523; 514/524; 558/390; 558/391
[58] Field of Search ................ 558/390, 391; 514/523, 514/524

[56] References Cited

U.S. PATENT DOCUMENTS

| | | | |
|---|---|---|---|
| 3,912,724 | 10/1975 | Begland | 558/391 X |
| 3,914,276 | 10/1975 | Begland | 558/391 |
| 4,002,616 | 1/1977 | Neumer | 200/240 G |

FOREIGN PATENT DOCUMENTS

| | | |
|---|---|---|
| 2500168 | 7/1975 | Fed. Rep. of Germany . |
| 2809022 | 9/1978 | Fed. Rep. of Germany . |
| 0157320 | 12/1975 | Japan .................................... 514/523 |
| 0147558 | 9/1982 | Japan .................................... 558/391 |

OTHER PUBLICATIONS

Robertson and Vaughan, Journal of the American Chemical Society, 80, (1958), pp. 2691-2693.
Hinkel et al, Journal of the Chemical Society (1937), pp. 1432-1437.
O. Bayer, Houben-Weyl, vol. VII/1, pp. 16-36, (1954).
Patent Abstracts of Japan, Mar. 28, 1977, C Section, vol. 1, #29 [abstract of Kokai No. 51-151325].
Chemical Abstracts, vol. 88, Jan. 16, 1978, 88:22162y; Kojima et al.
Chemical Abstracts, vol. 103, Jul. 8, 1985, 103:6273h, Moriya et al.
*The Journal of Organic Chemistry*, vol. 39, 1974, May–Aug.

*Primary Examiner*—Joseph Paul Brust

[57] ABSTRACT

A method for combating arachnida which comprises applying to arachnida and/or to a habitat thereof an effective pest combating amount of at least one derivative of a 2,3-diaminomaleonitrile of the formula

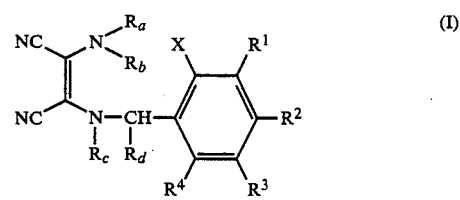

in which X represents hydrogen, halogen, halogenoalkyl or CN, $R^1$, $R^2$, $R^3$ and $R^4$ are defined or different and represent hydrogen, alkyl, alkoxy, halogen, CN, $NO_2$, dialkylamino, alkoxycarbonyl, alkylthio, alkylthionyl, alkylsulphonyl, OH, SH or $NH_2$, wherein $R_1$ and $R_b$ together represent the radical (II)

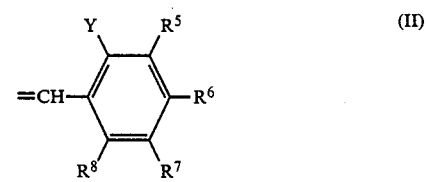

in which Y represents hydrogen, halogen, halogenoalkyl or CN, $R^5$, $R^6$, $R^7$ and $R^8$ are identical or different and represent hydrogen, alkyl, alkoxy, halogen, CN, $NO_2$, dialkylamino, alkoxycarbonyl, alkylthio, alkylthionyl, alkylsulphonyl, OH, SH or $NH_2$, and in which $R_c$ and $R_d$ together represent a chemical bond, or $R_a$ and $R_b$ together represent the radical (II), in which Y, $R^5$, $R^6$, $R^7$ and $R^8$ possess the meanings given above and in which $R_c$ and $R_d$ in each case represent hydrogen, or $R_a$, $R_b$, $R_c$ and $R_d$ in each case represent hydrogen, or $R_a$ represents hydrogen and $R_b$ represents the radical (II) in which Y, $R^5$, $R^6$, $R^7$ and $R^8$ possess the meanings given above and $R_c$ and $R_d$ represent hydrogen.

4 Claims, No Drawings

PEST-COMBATING AGENTS BASED ON DERIVATIVES OF 2,3-DIAMINOMALEONITRILE

The present invention relates to the use of derivatives of 2,3-diaminomaleonitrile, some of which are known. The invention furthermore relates to the preparation of new derivatives of 2,3-diaminomaleonitrile.

Derivatives of 2,3-diaminomaleonitrile have been disclosed in various literature sources. See, for example, U.S. Pat. No. 4,002,616, where bisanil derivatives are described, or see, for example, Onoda in Nippon Nogeikagaku Kaishi 36(2), 167–72 (1962), where monoanil derivatives of 2,3-diaminomaleonitrile are described, as they are in the publications of Robertson, Vaughan in *Journal of the American Chemical Society*, 80, 2691 (1958) and Hinkel et al., *Journal of the Chemical Society*, 1937, 1432.

Nothing has yet been disclosed, however, on the activity of the abovementioned classes of compound or other derivatives of 2,3-diaminomaleonitrile.

It has been found that the derivatives, some of which are known, of 2,3-diaminomaleonitrile of the general formula

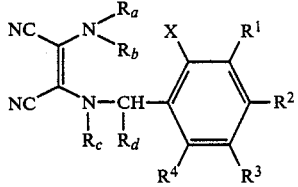
(I)

in which
x represents hydrogen, halogen, halogenoalkyl or CN, $R^1$, $R^2$, $R^3$ and $R^4$ can be identical or different and represent hydrogen, optionally substituted alkyl, optionally substituted alkoxy, halogen, CN, $NO_2$, optionally substituted dialkylamino, alkoxycarbonyl, optionally substituted alkylthio, optionally substituted alkylthionyl, optionally substituted alkylsulphonyl, OH, SH or $NH_2$, and the substituents $R_a$, $R_b$, $R_c$ and $R_d$ can in each case assume one of the following combinations of meaning A, B, C or D;

(A) $R_a$ and $R_b$ together represent the radical

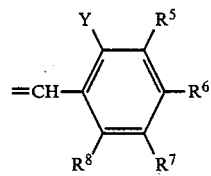

in which
Y represents hydrogen, halogen, halogenoalkyl or CN, $R^5$, $R^6$, $R^7$ and $R^8$ can be identical or different and represent hydrogen, optionally substituted alkyl, optionally substituted alkoxy, halogen, CN, $NO_2$, optionally substituted dialkylamino, alkoxycarbonyl, optionally substituted alkylthio, optionally substituted alkylthionyl, optionally substituted alkylsulphonyl, OH, SH or $NH_2$, and in which $R_c$ and $R_d$ together represent a chemical bond, (B) $R_a$ and $R_b$ together represent the radical

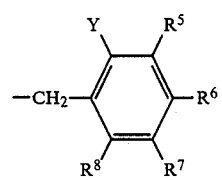

in which Y, $R^5$, $R^6$, $R^7$ and $R^8$ possess the meanings given under (A) and in which $R_c$ and $R_d$ in each case represent hydrogen, (C) $R_a$, $R_b$, $R_c$ and $R_d$ in each case represent hydrogen, (D) $R_a$ represents hydrogen and $R_b$ represents the radical

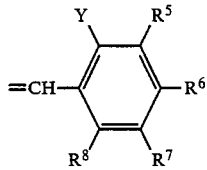

in which Y, $R^5$, $R^6$, $R^7$ and $R^8$ possess the meanings given under (A) and $R_c$ and $R_d$ represent hydrogen, possess a strongly marked activity against animal pests and in particular against arachnida.

The following related chemical structures $I_A$, $I_B$, $I_C$ and $I_D$ therefore result:

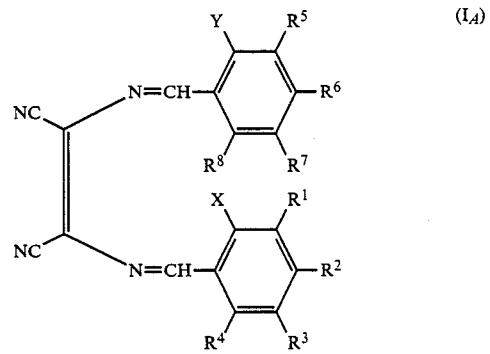
($I_A$)

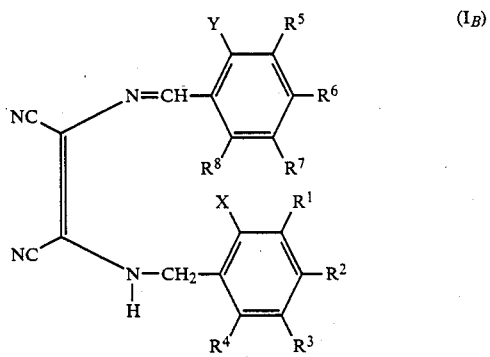
($I_B$)

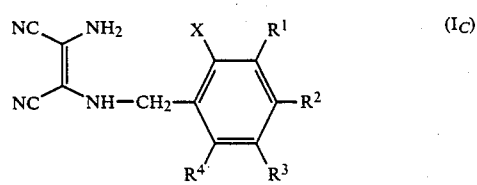
($I_C$)

-continued
and

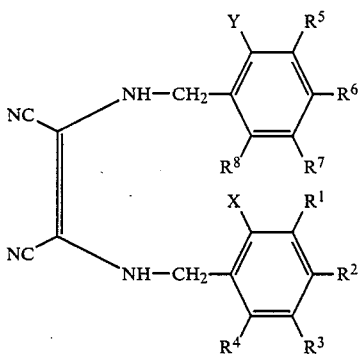

The compounds of the formulae (I$_B$), (I$_C$) and (I$_D$) are new substances. In general, it should be stated that the compounds of the general formula (I) can exist per se both in the cis form

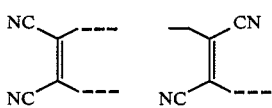

and also in the stereoisomeric trans form.

Preferably, the compounds of the general formula (I) exist in the cis form. Surprisingly, the compounds of the general formula (I) show a strongly pronounced activity against arachnida. Such an action of compounds of similar or identical structure from the prior art has hitherto not been disclosed.

The bisanils of the formula (I$_A$)

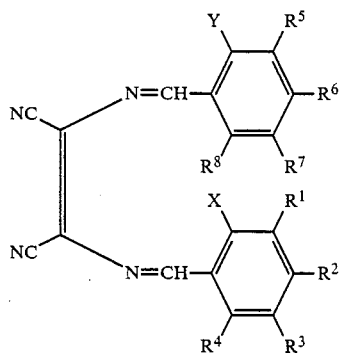

in which the radicals R$^1$ to R$^8$ and also X and Y possess the abovementioned meanings are obtained by reacting 2,3-diaminomaleonitrile ("DAMN") of the formula (II)

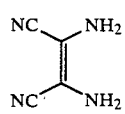

with an aldehyde of the formula (III)

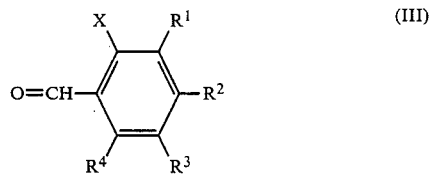

in which

X, R$^1$, R$^2$, R$^3$ and R$^4$ possess the abovementioned meanings, in equimolar amounts in a diluent to form the azomethine of the formula

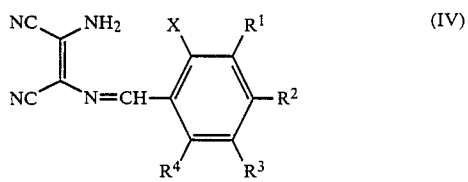

and then reacting this with the addition of a catalyst with a molar amount of an additional aldehyde of the formula (V)

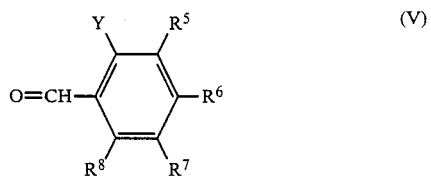

in which Y, R$^5$, R$^6$, R$^7$ and R$^8$ have the abovementioned meanings.

Furthermore, the symmetrical bisanils of the formula (VI)

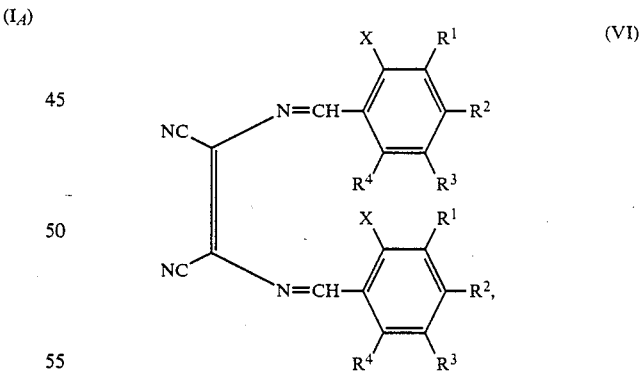

i.e., compounds of the formula I$_A$ for which: (X=Y, R$^1$=R$^5$, R$^2$=R$^6$, R$^3$=R$^7$, R$^4$=R$^8$), are obtained by reacting 1 mole of 2,3-diaminomaleonitrile (DAMN) of the formula (II)

with 2 moles of an aldehyde of the formula (III)

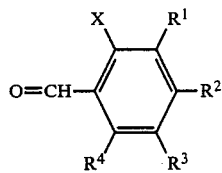

in which X, R$^1$, R$^2$, R$^3$ and R$^4$ have the abovementioned meanings in a diluent with the addition of a catalyst.

The compounds of the general formula (I$_A$) can exist in the stereoisomeric cis and/or trans forms. The compounds preferably exist in the cis form, however.

Formula (I$_A$) provides a general definition of the acaricidally active bisanils.

In formula (I$_A$), X and Y, which can be identical or different, preferably represent fluorine, chlorine, bromine, iodine, CF$_3$ or CN.

In the radicals R$^1$, R$^2$, R$^3$ and R$^4$ and also R$^5$, R$^6$, R$^7$ and R$^8$, which can likewise be identical or different, suitable substituents for alkyl, alkoxy, dialkylamino, alkylthio, alkylthionyl and alkylsulphonyl are preferably: halogen, in particular fluorine, chlorine and bromine, and also OH and NH$_2$.

Preferred compounds are those of the formula (I$_A$) in which

X and R$^4$ and also Y and R$^8$ can be identical or different and represent hydrogen, fluorine, chlorine, bromine, iodine, CF$_3$ or CN, R$^1$, R$^2$ and R$^3$ and also R$^5$, R$^6$ and R$^7$ can be identical or different and represent hydrogen, alkyl (C$_1$-C$_4$), halogenoalkyl(C$_1$-C$_4$), alkoxy(C$_1$-C$_4$), halogenoalkoxy(C$_1$-C$_4$), halogen, CN, NO$_2$, dialkyl(C$_1$-C$_4$)amino, alkoxy(C$_1$-C$_4$)carbonyl, alkyl(-C$_1$-C$_4$)thio, alkyl(C$_1$-C$_4$)thionyl, dihalogenoalkyl(-C$_1$-C$_4$)amino, alkyl(C$_1$-C$_4$)sulphonyl, OH, SH or NH$_2$.

Particularly preferred compounds are those of the general formula (I$_{A'}$)

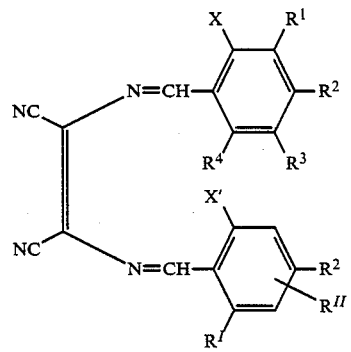

in which

X, R$^1$, R$^2$, R$^3$ and R$^4$ have the abovementioned meanings and X' and R$^I$ can be identical or different and represent fluorine, chlorine, bromine, iodine or CF$_3$ and R$^{II}$ represents hydogen, chlorine, bromine, iodine, cyano, nitro, methyl, ethyl, n- and i-proply, n-, i-, s- and t-butyl, methoxy, ethoxy, methoxycarbonyl, ethoxycarbonyl, trifluoromethyl, trichloromethyl, pentafluoroethyl, trifluoroethyl, trifluoromethylsulphonyl, trifluoromethoxy, trichloromethoxy, pentafluoroethoxy, dimetyhlamino, diethylamino, di-β-chloroethylamino or di-β-hydroxyethylamino.

Very particularly preferred compounds are those of the formula (I$_{A''}$)

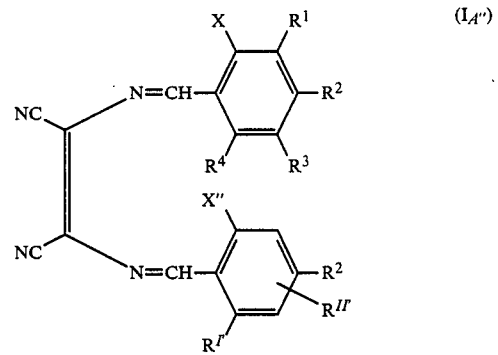

in which

X, R$^1$, R$^2$, R$^3$ and R$^4$ have the abovementioned meanings and X" and R$^{I'}$ can be identical or different and represent chlorine or bromine and R$^{II}$ represents chlorine, bromine, iodine, hydrogen, cyano, nitro, methyl, ethyl, n- and i-propyl, methoxy, ethoxy, methoxycarbonyl, ethoxycarbonyl, trifluoromethyl, trichloromethyl, dimethylamino, diethylamino or trifluoromethylsulphone.

Exceedingly preferred compounds are those of the formula (I$_{A'''}$)

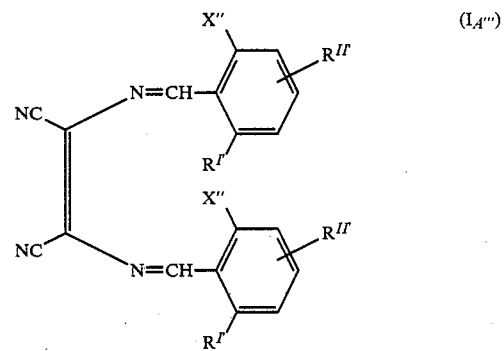

in which

X" and R$^{I'}$ can be identical or different and represent chlorine or bromine and R$^{II}$ represents chlorine, bromine, iodine, hydrogen, cyano, nitro, methyl, ethyl, n- and i-propyl, methoxy, ethoxy, methoxycarbonyl, ethoxycarbonyl, trifluoromethyl, trichloromethyl, dimethylamino, diethylamino or trifluoromethylsulphone.

Compounds of very particular interest are those of the formula (I$_{A''''}$)

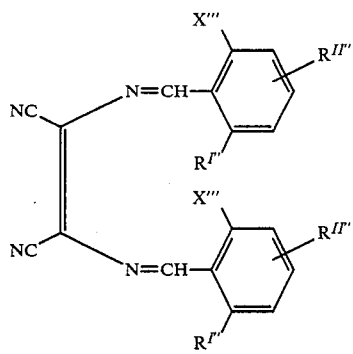

(I$_{A''''}$)

in which
X''' and R$^{I'}$ can be identical or different and represent chlorine or bromine and
R$^{II'}$ represents hydrogen, chlorine, bromine, methyl, cyano, trichloromethyl, trifluoromethyl, methoxy, trifluoromethoxy, trichloromethoxy or trifluoromethylsulphone.

Exceedingly preferred compounds are those of the formula (I$_{A'''''}$)

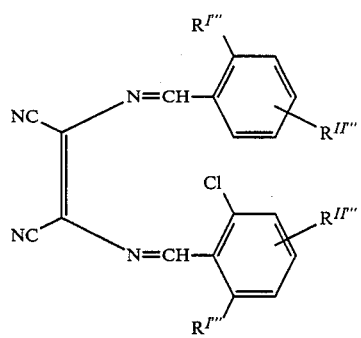

(I$_{A'''''}$)

in which
R$^{I'''}$ represents chlorine or bromine and
R$^{II'''}$ represents hydrogen, chlorine, methyl, trichloromethyl, methoxy, trichloromethoxy or trifluoromethoxy.

If, for example, 2,3-diaminomaleonitrile (DAMN) and 2,6-dichlorobenzaldehyde are used as starting compounds, the corresponding bisanil can be prepared as follows:

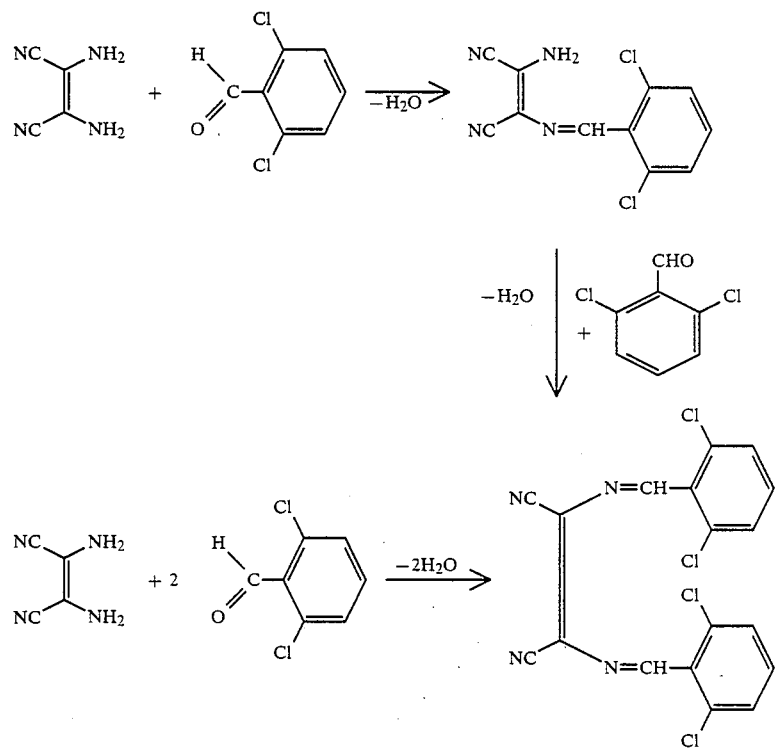

Formulae (III) and (V) provide a general definition of the aldehydes required as starting materials for carrying out the process for the preparation of the bisanils (I$_A$). They are essentially known compounds. In this respect see, for example, O. Bayer, in *Houben-Weyl*, Vol. VII/1, 16–36, (1954).

The other starting compound 2,3-diaminomaleonitrile is likewise known in the literature and commercially obtainable.

Suitable diluents for carrying out the process for the preparaton of the utilizable compounds of the formulae (I$_A$) or (VI) according to the invention are preferably polar organic solvents such as, for example, alcohols (in particular methanol, ethanol, propanol (n and i)), dimethylformamide (DMF), dimethyl sulphoxide (DMSO), hexemethylphosphoric acid triamide (HMPT) or acetonitrile.

The reaction temperature is generally in the range between about 0° C. up to a maximum of the boiling point of the particular solvent, in particular the reaction is carried out at temperatures of about 20° to about 100° C.

The reaction is preferably carried out at atmospheric pressure.

Preferred catalysts used for the reaction of the compounds of the formula (VI) with molar amounts of the aldehyde of the formula (V) are: inorganic or organic acids or derivatives. Examples which may be mentioned are: hydrochloric acid, hydrobromic acid, hydroiodic acid, sulphuric acid, boron trifluoride, tetrafluoroboric acid, perchloric acid, methanesulphonic acid, trifluoromethanesulphonic acid, p-toluenesulphonic acid, phosphoric acid, phosphorus pentoxide, formic acid, acetic acid, propionic acid, hydrogen chloride and hydrogen bromide.

0.001 to 2 moles of catalyst per mole of aldehyde of the formula (V) are employed here, preferably 0.01 to 1 mole of catalyst per mole of aldehyde of the formula (V).

The abovementioned catalysts in the abovementioned amount ratios are preferably employed for the direct reaction of 2,3-diaminomaleonitrile with 2 moles of aldehyde of the formula (III) in order to obtain the symmetrical bisanils of the formula (VI).

The compounds of the formula (IV)

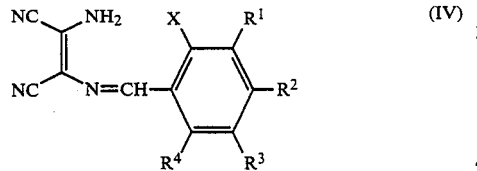
(IV)

in which X, $R^1$, $R^2$, $R^3$ and $R^4$ possess the abovementioned meanings, are the subject of a previously filed patent application, i.e. German patent application P 3704154.1 filed on Feb. 11, 1987.

The compounds of the formula (IV) are thus accessible by reacting the known 2,3-diaminomaleonitrile of the formula

(II)

with an aldehyde of the formula

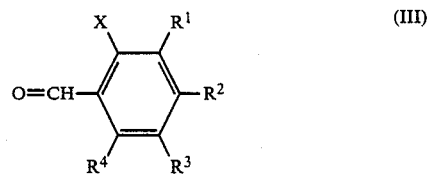
(III)

in which X, $R^1$, $R^2$, $R^3$ and $R^4$ possess the abovementioned meanings, in equimolar amount in a suitable (preferably polar organic) solvent and working up the reaction products by methods known per se.

The following bisanils of the formula ($I_A$)

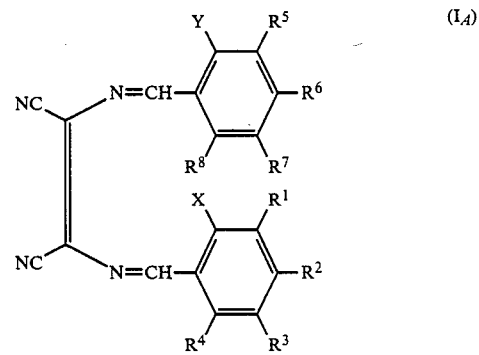
($I_A$)

may be mentioned individually in addition to the compounds mentioned in the preparation examples:

| X | $R^1$ | $R^2$ | $R^3$ | $R^4$ | Y | $R^5$ | $R^6$ | $R^7$ | $R^8$ |
|---|---|---|---|---|---|---|---|---|---|
| H | H | H | H | H | Cl | H | H | H | H |
| H | H | H | H | H | Cl | H | Cl | H | H |
| H | H | H | H | H | Cl | H | Cl | H | Cl |
| H | H | H | H | H | Cl | H | H | H | F |
| H | H | H | H | H | H | $CF_3$ | H | H | H |
| H | H | H | H | H | $CF_3$ | H | H | H | $CF_3$ |
| H | H | H | H | H | Cl | $OCF_3$ | Cl | H | Cl |
| H | H | H | H | H | F | F | F | F | F |
| H | H | H | H | H | F | F | OH | F | F |
| H | H | H | H | H | $CF_3$ | H | F | H | $CF_3$ |
| H | H | H | H | H | Cl | H | F | H | Cl |
| H | H | H | H | H | Br | H | H | H | Cl |
| H | H | H | H | H | Cl | H | $CF_3$ | H | H |
| H | H | H | H | H | Cl | Cl | $CF_3$ | H | Cl |
| H | H | H | H | H | Cl | H | $COOCH_3$ | H | Cl |
| H | H | H | H | H | Cl | H | $OCH_3$ | H | Cl |
| H | H | H | H | H | Cl | H | $SCF_3$ | H | Cl |
| H | H | H | H | H | Cl | H | $SO_2CF_3$ | H | Cl |
| H | H | H | H | H | Cl | H | $CH_3$ | H | H |
| H | H | H | H | H | Br | H | H | H | F |
| H | H | H | H | H | H | $OCH_3$ | OH | H | H |
| H | H | H | H | H | H | H | Cl | $NO_2$ | H |
| H | H | H | H | H | CN | H | H | H | Cl |
| H | H | H | H | H | H | H | CN | H | H |
| H | H | H | H | H | H | Br | OH | $OCH_3$ | H |
| Cl | H | H | H | H | Cl | H | H | H | Cl |

-continued

| X | R¹ | R² | R³ | R⁴ | Y | R⁵ | R⁶ | R⁷ | R⁸ |
|---|----|----|----|----|---|----|----|----|----|
| Cl | H | H | H | H | Cl | H | Cl | H | H |
| Cl | H | H | H | H | Cl | H | CH₃ | H | H |
| Cl | H | H | H | H | CN | H | H | H | H |
| Cl | H | H | H | H | Br | H | Br | H | Br |
| Cl | H | H | H | H | Br | H | H | H | Cl |
| Cl | H | H | H | H | Cl | H | F | H | Cl |
| Cl | H | H | H | H | CF₃ | H | H | H | CF₃ |
| Cl | H | H | H | H | H | CF₃ | H | H | H |
| Cl | H | H | H | H | CF₃ | H | F | H | CF₃ |
| Cl | H | H | H | H | Cl | H | H | H | F |
| Cl | H | H | H | H | Cl | OCF₃ | Cl | H | Cl |
| Cl | H | H | H | H | H | Cl | H | Cl | OH |
| H | Cl | H | H | H | Cl | H | H | H | Cl |
| H | Cl | H | H | H | Cl | H | Cl | H | H |
| H | Cl | H | H | H | Cl | H | CH₃ | H | H |
| H | Cl | H | H | H | CN | H | H | H | H |
| H | Cl | H | H | H | Br | H | H | H | Br |
| H | Cl | H | H | H | Br | H | Br | H | Br |
| H | Cl | H | H | H | Br | H | H | H | Cl |
| H | Cl | H | H | H | Cl | H | H | H | F |
| H | Cl | H | H | H | Cl | H | F | H | Cl |
| H | Cl | H | H | H | CF₃ | H | H | H | CF₃ |
| H | Cl | H | H | H | H | CF₃ | H | H | H |
| H | Cl | H | H | H | Cl | H | Cl | OCF₃ | Cl |
| H | Cl | H | H | H | H | Cl | H | Cl | OH |
| H | H | Cl | H | H | Cl | H | H | H | Cl |
| H | H | Cl | H | H | Cl | H | Cl | H | H |
| H | H | Cl | H | H | Cl | H | CH₃ | H | H |
| H | H | Cl | H | H | CN | H | H | H | H |
| H | H | Cl | H | H | Br | H | H | H | Br |
| H | H | Cl | H | H | Br | H | Br | H | Br |
| H | H | Cl | H | H | Br | H | H | H | Cl |
| H | H | Cl | H | H | Cl | H | F | H | Cl |
| H | H | Cl | H | H | CF₃ | H | H | H | CF₃ |
| H | H | Cl | H | H | H | CF₃ | H | H | H |
| H | H | Cl | H | H | Cl | H | Cl | OCF₃ | Cl |
| H | H | Cl | H | H | H | Cl | H | Cl | OH |
| Cl | H | H | H | Cl | Cl | H | H | H | Cl |
| Cl | H | H | H | Cl | Cl | H | Cl | H | H |
| Cl | H | H | H | Cl | Cl | H | CH₃ | H | H |
| Cl | H | H | H | Cl | CN | H | H | H | H |
| Cl | H | H | H | Cl | Br | H | H | H | Br |
| Cl | H | H | H | Cl | Br | H | Br | H | Br |
| Cl | H | H | H | Cl | Br | H | H | H | Cl |
| Cl | H | H | H | Cl | Cl | H | H | H | F |
| Cl | H | H | H | Cl | Cl | H | F | H | Cl |
| Cl | H | H | H | Cl | CF₃ | H | H | H | CF₃ |
| Cl | H | H | H | Cl | H | CF₃ | H | H | H |
| Cl | H | H | H | Cl | Cl | H | Cl | OCF₃ | Cl |
| Cl | H | H | H | Cl | H | Cl | H | Cl | OH |
| Cl | H | Cl | H | H | Cl | H | H | H | Cl |
| Cl | H | Cl | H | H | Cl | H | Cl | H | H |
| Cl | H | Cl | H | H | Cl | H | CH₃ | H | H |
| Cl | H | Cl | H | H | CN | H | H | H | H |
| Cl | H | Cl | H | H | Br | H | H | H | Br |
| Cl | H | Cl | H | H | Br | H | Br | H | Br |
| Cl | H | Cl | H | H | Br | H | H | H | Cl |
| Cl | H | Cl | H | H | Cl | H | H | H | F |
| Cl | H | Cl | H | H | Cl | H | F | H | Cl |
| Cl | H | Cl | H | H | CF₃ | H | H | H | CF₃ |
| Cl | H | Cl | H | H | H | CF₃ | H | H | H |
| Cl | H | Cl | H | H | Cl | H | Cl | OCF₃ | Cl |
| Cl | H | Cl | H | H | H | Cl | H | Cl | OH |
| H | CF₃ | H | H | H | Cl | H | H | H | Cl |
| H | CF₃ | H | H | H | Cl | H | Cl | H | H |
| H | CF₃ | H | H | H | Cl | H | CH₃ | H | H |
| H | CF₃ | H | H | H | CN | H | H | H | H |
| H | CF₃ | H | H | H | Br | H | H | H | Br |
| H | CF₃ | H | H | H | Br | H | Br | H | Br |
| H | CF₃ | H | H | H | Br | H | H | H | Cl |
| H | CF₃ | H | H | H | Cl | H | H | H | F |
| H | CF₃ | H | H | H | Cl | H | F | H | Cl |
| H | CF₃ | H | H | H | CF₃ | H | H | H | CF₃ |
| H | CF₃ | H | H | H | H | CF₃ | H | H | H |
| H | CF₃ | H | H | H | Cl | H | Cl | OCF₃ | Cl |
| H | CF₃ | H | H | H | H | Cl | H | Cl | OH |
| Cl | H | H | H | F | Cl | H | H | H | Cl |
| Cl | H | H | H | F | Cl | H | Cl | H | H |
| Cl | H | H | H | F | Cl | H | CH₃ | H | H |

-continued

| X | R¹ | R² | R³ | R⁴ | Y | R⁵ | R⁶ | R⁷ | R⁸ |
|---|----|----|----|----|---|----|----|----|----|
| Cl | H | H | H | F | CN | H | H | H | H |
| Cl | H | H | H | F | Br | H | H | H | Br |
| Cl | H | H | H | F | Br | H | Br | H | Br |
| Cl | H | H | H | F | Br | H | H | H | Cl |
| Cl | H | H | H | F | Cl | H | H | H | F |
| Cl | H | H | H | F | Cl | H | F | H | Cl |
| Cl | H | H | H | F | CF₃ | H | H | H | CF₃ |
| Cl | H | H | H | F | H | CF₃ | H | H | H |
| Cl | H | H | H | F | Cl | H | Cl | OCF₃ | Cl |
| Cl | H | H | H | F | H | Cl | H | Cl | OH |
| CF₃ | H | H | H | CF₃ | Cl | H | H | H | H |
| CF₃ | H | H | H | CF₃ | H | Cl | Cl | H | H |
| CF₃ | H | H | H | CF₃ | H | CF₃ | H | H | H |
| CF₃ | H | H | H | CF₃ | H | Cl | H | Cl | OH |
| CF₃ | H | H | H | CF₃ | Cl | H | Cl | H | H |
| CF₃ | H | H | H | CF₃ | Cl | H | H | H | Cl |
| Cl | H | Cl | OCF₃ | Cl | Cl | H | H | H | H |
| Cl | H | Cl | OCF₃ | Cl | Cl | H | H | H | Cl |
| Cl | H | Cl | OCF₃ | Cl | Cl | H | Cl | H | H |
| Cl | H | Cl | OCF₃ | Cl | H | Cl | Cl | H | H |
| Cl | H | Cl | OCF₃ | Cl | H | CF₃ | H | H | H |
| Cl | H | Cl | OCF₃ | Cl | H | OCH₃ | OH | Br | H |
| H | Cl | Cl | H | H | Cl | H | H | H | Cl |
| Cl | H | CH₃ | H | H | Cl | H | H | H | H |
| Cl | H | CH₃ | H | H | H | CF₃ | H | H | H |
| Cl | H | CH₃ | H | H | Cl | H | H | H | Cl |
| Cl | H | CH₃ | H | H | Cl | H | Cl | H | H |
| Cl | H | CH₃ | H | H | H | Cl | H | Cl | OH |
| Cl | H | CF₃ | H | Cl | Cl | H | Cl | H | H |
| Cl | H | CF₃ | H | Cl | H | CF₃ | H | H | H |
| Cl | H | CF₃ | H | Cl | H | Cl | H | H | Cl |
| Cl | H | CF₃ | H | Cl | H | Cl | H | Cl | OH |
| Cl | H | CF₃ | H | Cl | H | NO₂ | H | H | H |
| Cl | CF₃ | Cl | H | H | CF₃ | H | CH₃ | H | CH₃ |
| Cl | CF₃ | Cl | H | H | Cl | H | CH₃ | H | H |
| H | H | N(CH₃)₂ | H | H | Cl | H | H | H | Cl |

The new benzyl-benzylidene derivatives of 2,3-diaminomaleonitrile of the formula ($I_B$)

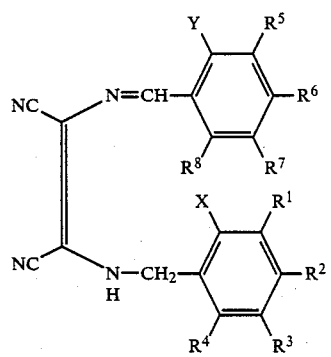

in which X, Y, R¹, R², R³, R⁴, R⁵, R⁶, R⁷ and R⁸ have the meanings given under formula ($I_A$), are obtained when benzyl compounds of the general formula

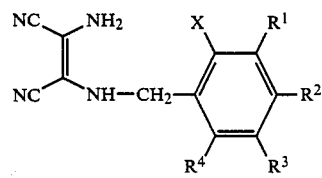

are reacted with an aldehyde of the formula (V)

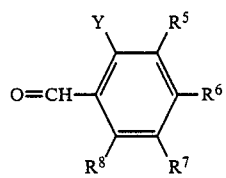

in which Y, R⁵, R⁶, R⁷ and R⁸ have the abovementioned meanings in equimolar amount in a suitable diluent.

Surprisingly, the compounds of the formula ($I_B$) show an acaricidal activity. Such an action was hitherto unknown for the benzyl-benzylidene compounds of diaminomalelonitrile class of substances. The compounds according to the invention therefore represent an enrichment of the prior art.

The compounds of the general formula ($I_B$) can exist in the stereoisomeric cis and/or trans forms, however the compounds preferably exist in the cis form.

In the formula ($I_B$), X and Y preferably represent hydrogen, fluorine, chlorine, bromine, iodine, CF₃ or CN.

In the radicals R¹, R², R³ and R⁴ or R⁵, R⁶, R⁷ and R⁸, suitable substituents for alkyl, alkoxy, dialkylamino, alkylthio, alkylthionyl or alkylsulphonyl are: halogen, in particular fluorine, chlorine and bromine and also OH and NH₂.

Preferred compounds are those of the formula ($I_B$) in which

X and R⁴ and also Y and R⁸ can be identical or different and represent hydrogen, fluorine, chlorine, bromine, iodine, CF₃ or CN, $R^1$, $R^2$ and $R^3$ and also $R^5$, $R^6$ and $R^7$ can be identical or different and represents hydrogen, alkyl($C_1$-$C_4$), halogenoalkyl($C_1$-$C_4$), alkoxy($C_1$-$C_4$), halogenoalkoxy($C_1$-$C_4$), halogen, CN, $NO_2$, dialkyl($C_1$-$C_4$)amino, alkoxy($C_1$-$C_4$)carbonyl, alkyl($C_1$-$C_4$)thio, alkyl($C_1$-$C_4$)thionyl, dihalogenoalkyl($C_1$-$C_4$)amino, alkyl($C_1$-$C_4$)sulphonyl, OH, SH, or $NH_2$.

Particularly preferred compounds are those of the general formula ($I_{B'}$)

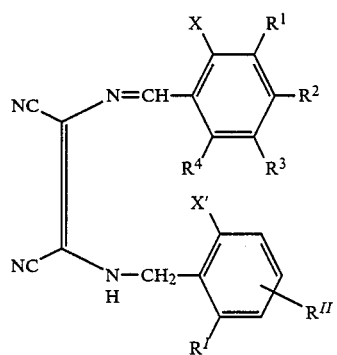

in which X, $R^1$, $R^2$, $R^3$ and $R^4$ have the abovementioned meanings and

X' and $R^I$ can be identical or different and represent hydrogen, fluorine, chlorine, bromine, iodine or $CF_3$ and $R^{II}$ represents hydrogen, chlorine, bromine, iodine, cyano, nitro, methyl, ethyl, n- and i-propyl, n-, i-, s- and t-butyl, methoxy, ethoxy, methoxycarbonyl, ethoxycarbonyl, trifluoromethyl, trichloromethyl, pentafluoroethyl, trifluoroethyl, trifluoromethylsulphone, trifluoromethoxy, trichloromethoxy, pentafluoroethoxy, dimethylamino, diethylamino, di-β-chloroethylamino and di-β-hydroxyethylamino.

Very particularly preferred compounds are those of the formula ($I_{B''}$)

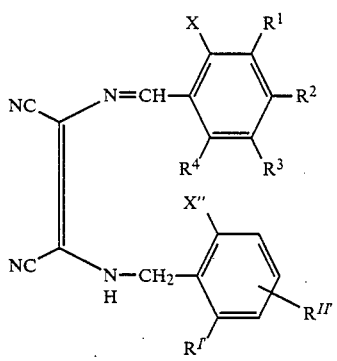

in which X, $R^1$, $R^2$, $R^3$ and $R^4$ have the abovementioned meanings and

X" and $R^I$ can be identical or different and represent hydrogen, chlorine or bromine and $R^{II}$ represents chlorine, bromine, iodine, hydrogen, cyano, nitro, methyl, ethyl, n- and i-propyl, methoxy, ethoxy, methoxycarbonyl, ethoxycarbonyl, trifluoromethyl, trichloromethyl, dimethylamino, diethylamino or trifluoromethylsulphone.

Very particularly preferred compounds are furthermore those of the formula ($I_{B'''}$)

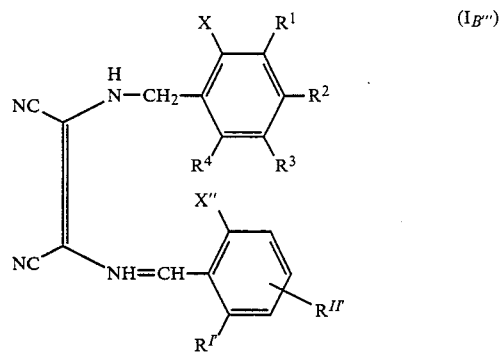

in which X, $R^1$, $R^2$, $R^3$ and $R^4$ have the abovementioned meanings and

X" and $R^I$ can be identical or different and represent hydrogen, chlorine or bromine and $R^{II}$ represents chlorine, bromine, iodine, hydrogen, cyano, nitro, methyl, ethyl, n- and i-propyl, methoxy, ethoxy, methoxycarbonyl, ethoxycarbonyl, trifluoromethyl, trichloromethyl, dimethylamino, diethylamino or trifluoromethylsulphone.

Exceedingly preferred compounds are those of the formula ($I_{B''''}$)

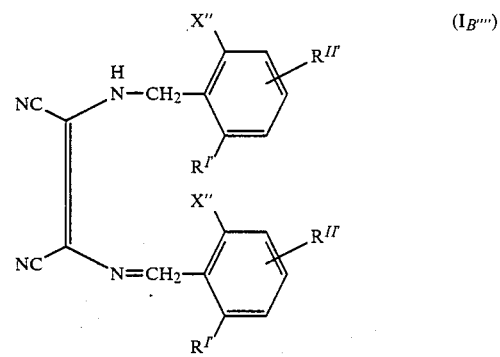

in which

X" and $R^I$ can be identical or different and represent hydrogen, chlorine or bromine and $R^{II}$ represents chlorine, bromine, iodine, hydrogen, cyano, nitro, methyl, ethyl, n- and i-propyl, methoxy, ethoxy, methoxycarbonyl, ethoxycarbonyl, trifluoromethyl, trichloromethyl, dimethylamino, diethylamino and trifluoromethylsulphone.

Extremely preferred compounds are those of the formula ($I_{B'''''}$)

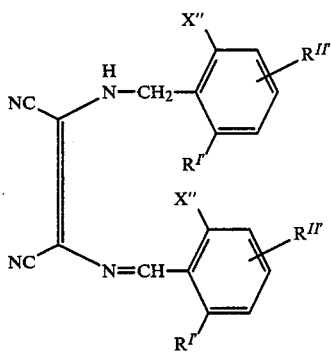

(I_B''''')

in which

X'' and $R^{I'}$ can be identical or different and represent hydrogen, chlorine or bromine and $R^{II'}$ represents chlorine, bromine, iodine, hydrogen, cyano, nitro, methyl, ethyl, n- and i-propyl, methoxy, ethoxy, methoxycarbonyl, ethoxycarbonyl, trifluoromethyl, trichloromethyl, dimethylamino, diethylalmino or trifluoromethylsulphone.

Compounds of very particular interest are those of the formula ($I_B$VI)

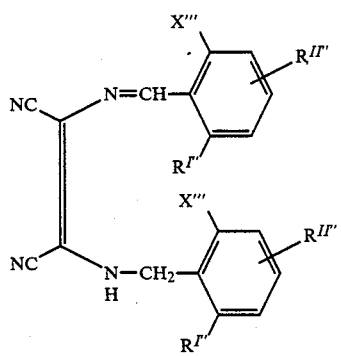

(I_BVI)

in which

X''' and $R^{I''}$ can be identical or different and represent hydrogen, chlorine or bromine and $R^{II''}$ represents hydrogen, chlorine, bromine, methyl, cyano, trifluoromethyl, methoxy, trifluoromethoxy, trichloromethoxy or trifluoromethylsulphone.

Exceedingly preferred compounds are those of the general formula ($I_B$VII)

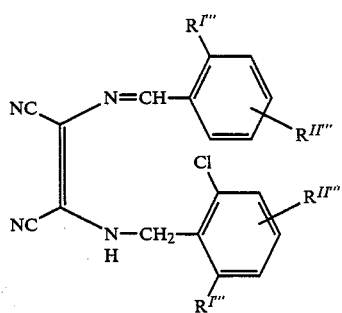

(I_BVII)

in which $R^{I'''}$ represents chlorine or bromine and $R^{II'''}$ represents hydrogen, chlorine, methyl, trichloromethyl, methoxy, trichloromethoxy or trifluoromethoxy.

Compounds of very particular interest are those of the formula ($I_B$VIII)

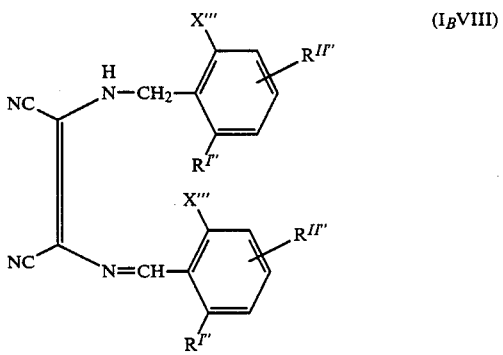

(I_BVIII)

in which

X'''' and $R^{I''}$ can be identical or different and represent hydrogen, chlorine or bromine and $R^{II''}$ represents hydrogen, chlorine, bromine, methyl, cyano, trifluoromethyl, methoxy, trifluoromethoxy, trichloromethoxy or trifluoromethylsulphone.

Exceedingly preferred compounds are those of the general formula ($I_B$IX)

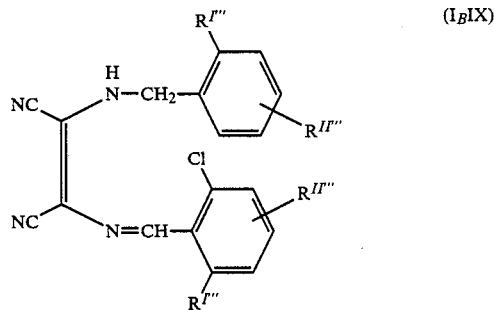

(I_BIX)

in which $R^{I'''}$ represents chlorine or bromine and $R^{II'''}$ represents hydrogen, chlorine, methyl, trichloromethyl, methoxy, trichloromethoxy or trifluoromethoxy.

If, for example, the 2,4-dichlorobenzyl compound of 2,3-diaminomaleonitrile and 2,6-dichlorobenzaldehyde are used as starting compounds, then the preparation process for obtaining the compounds $I_B$ can be represented as follows:

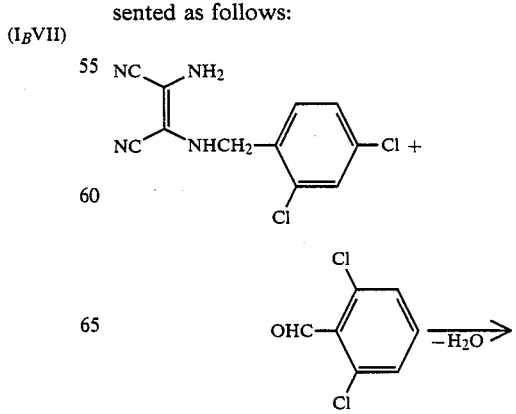

-continued

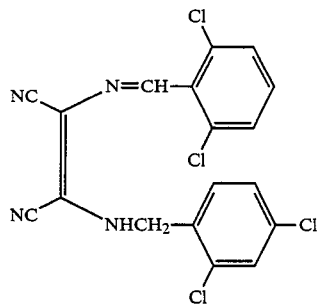

Formula (V) provides a general definition of the aldehydes required as starting materials for carrying out the process according to the invention. Essentially, they are known compounds. For this see, for example, O. Bayer, in *Houben-Weyl*, Vol. VII/1, p. 16-36, (1954).

Suitable diluents for carrying out the process according to the invention are preferably polar organic solvents such as, for example, alcohols (in particular methanol, ethanol, propanol (n and i)) dimethylformamide (DMF), dimethyl sulphoxide (DMSO), hexamethylphosphoric acid triamide (HMPT) and acetonitrile.

The reaction temperature is generally in the range between about 0° C. up to a maximum of the boiling point of the respective solvent; in particular the reaction is carried out at temperatures of about 20 to about 100° C.

The reaction is preferably carried out at atmospheric pressure.

When carrying out the process according to the invention, equimolar amounts of the reactants ($I_C$) and (V) are preferably reacted with one another. However, a slight excess of one of the two reactants can also be used.

In a preferred embodiment, the two reactants are combined in the diluent at room temperature and then heated to reflux.

Working up is by customary methods, the reaction product preferably being filtered off with suction after cooling and worked up by methods known per se.

The following benzyl-benzylidene compounds of the formula ($I_B$)

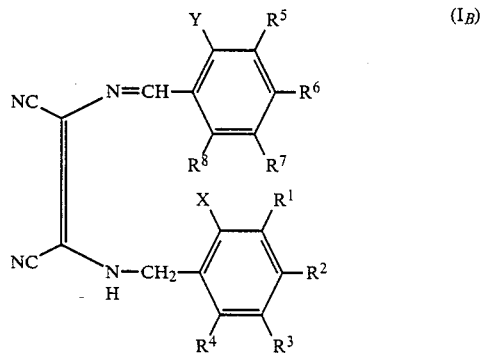

may be mentioned individually in addition to the compounds mentioned in the preparation examples:

| X  | $R^1$ | $R^2$ | $R^3$ | $R^4$ | Y   | $R^5$ | $R^6$    | $R^7$  | $R^8$ |
|----|-------|-------|-------|-------|-----|-------|----------|--------|-------|
| H  | H     | H     | H     | H     | Cl  | H     | H        | H      | H     |
| H  | H     | H     | H     | H     | Cl  | H     | Cl       | H      | H     |
| H  | H     | H     | H     | H     | Cl  | H     | Cl       | H      | Cl    |
| H  | H     | H     | H     | H     | Cl  | H     | H        | H      | F     |
| H  | H     | H     | H     | H     | H   | $CF_3$ | H        | H      | H     |
| H  | H     | H     | H     | H     | $CF_3$ | H  | H        | H      | $CF_3$ |
| H  | H     | H     | H     | H     | Cl  | $OCF_3$ | Cl     | H      | Cl    |
| H  | H     | H     | H     | H     | F   | F     | F        | F      | F     |
| H  | H     | H     | H     | H     | F   | F     | OH       | F      | F     |
| H  | H     | H     | H     | H     | $CF_3$ | H  | F        | H      | $CF_3$ |
| H  | H     | H     | H     | H     | Cl  | H     | F        | H      | Cl    |
| H  | H     | H     | H     | H     | Br  | H     | H        | H      | Cl    |
| H  | H     | H     | H     | H     | Cl  | H     | $CF_3$   | H      | H     |
| H  | H     | H     | H     | H     | Cl  | Cl    | $CF_3$   | H .    | Cl    |
| H  | H     | H     | H     | H     | Cl  | H     | $COOCH_3$ | H     | Cl    |
| H  | H     | H     | H     | H     | Cl  | H     | $OCH_3$  | H      | Cl    |
| H  | H     | H     | H     | H     | Cl  | H     | $SCF_3$  | H      | Cl    |
| H  | H     | H     | H     | H     | Cl  | H     | $SO_2CF_3$ | H    | Cl    |
| H  | H     | H     | H     | H     | Cl  | H     | $CH_3$   | H      | H     |
| H  | H     | H     | H     | H     | Br  | H     | H        | H      | F     |
| H  | H     | H     | H     | H     | H   | $OCH_3$ | OH     | H      | H     |
| H  | H     | H     | H     | H     | H   | H     | Cl       | $NO_2$ | H     |
| H  | H     | H     | H     | H     | CN  | H     | H        | H      | Cl    |
| H  | H     | H     | H     | H     | H   | H     | CN       | H      | H     |
| H  | H     | H     | H     | H     | H   | Br    | OH       | $OCH_3$ | H    |
| Cl | H     | H     | H     | H     | Cl  | H     | H        | H      | Cl    |
| Cl | H     | H     | H     | H     | Cl  | H     | Cl       | H      | H     |
| Cl | H     | H     | H     | H     | Cl  | H     | $CH_3$   | H      | H     |
| Cl | H     | H     | H     | H     | CN  | H     | H        | H      | H     |
| Cl | H     | H     | H     | H     | Br  | H     | Br       | H      | Br    |
| Cl | H     | H     | H     | H     | Br  | H     | H        | H      | Cl    |
| Cl | H     | H     | H     | H     | Cl  | H     | F        | H      | Cl    |
| Cl | H     | H     | H     | H     | $CF_3$ | H  | H        | H      | $CF_3$ |
| Cl | H     | H     | H     | H     | H   | $CF_3$ | H       | H      | H     |
| Cl | H     | H     | H     | H     | $CF_3$ | H  | F        | H      | $CF_3$ |
| Cl | H     | H     | H     | H     | Cl  | H     | H        | H      | F     |
| Cl | H     | H     | H     | H     | Cl  | $OCF_3$ | Cl     | H      | Cl    |
| Cl | H     | H     | H     | H     | H   | Cl    | H        | Cl     | OH    |
| H  | Cl    | H     | H     | H     | Cl  | H     | H        | H      | Cl    |
| H  | Cl    | H     | H     | H     | Cl  | H     | Cl       | H      | H     |

-continued

| X | R¹ | R²' | R³ | R⁴ | Y | R⁵ | R⁶ | R⁷ | R⁸ |
|---|----|----|----|----|---|----|----|----|----|
| H | Cl | H | H | H | Cl | H | CH₃ | H | H |
| H | Cl | H | H | H | CN | H | H | H | H |
| H | Cl | H | H | H | Br | H | H | H | Br |
| H | Cl | H | H | H | Br | H | Br | H | Br |
| H | Cl | H | H | H | Br | H | H | H | Cl |
| H | Cl | H | H | H | Cl | H | H | H | F |
| H | Cl | H | H | H | Cl | H | F | H | Cl |
| H | Cl | H | H | H | CF₃ | H | H | H | CF₃ |
| H | Cl | H | H | H | H | CF₃ | H | H | H |
| H | Cl | H | H | H | Cl | H | Cl | OCF₃ | Cl |
| H | Cl | H | H | H | H | Cl | H | Cl | OH |
| H | H | Cl | H | H | Cl | H | H | H | Cl |
| H | H | Cl | H | H | Cl | H | Cl | H | H |
| H | H | Cl | H | H | Cl | H | Cl | H | Cl |
| H | H | Cl | H | H | Cl | H | CH₃ | H | H |
| H | H | Cl | H | H | CN | H | H | H | H |
| H | H | Cl | H | H | Br | H | H | H | Br |
| H | H | Cl | H | H | Br | H | Br | H | Br |
| H | H | Cl | H | H | Br | H | H | H | Cl |
| H | H | Cl | H | H | Cl | H | H | H | F |
| H | H | Cl | H | H | Cl | H | F | H | Cl |
| H | H | Cl | H | H | CF₃ | H | H | H | CF₃ |
| H | H | Cl | H | H | H | CF₃ | H | H | H |
| H | H | Cl | H | H | Cl | H | Cl | OCF₃ | Cl |
| H | H | Cl | H | H | H | Cl | H | Cl | OH |
| Cl | H | H | H | Cl | Cl | H | H | H | Cl |
| Cl | H | H | H | Cl | Cl | H | Cl | H | H |
| Cl | H | H | H | Cl | Cl | H | CH₃ | H | H |
| Cl | H | H | H | Cl | CN | H | H | H | H |
| Cl | H | H | H | Cl | Br | H | H | H | Br |
| Cl | H | H | H | Cl | Br | H | Br | H | Br |
| Cl | H | H | H | Cl | Br | H | H | H | Cl |
| Cl | H | H | H | Cl | Cl | H | H | H | F |
| Cl | H | H | H | Cl | Cl | H | F | H | Cl |
| Cl | H | H | H | Cl | CF₃ | H | H | H | CF₃ |
| Cl | H | H | H | Cl | H | CF₃ | H | H | H |
| Cl | H | H | H | Cl | Cl | H | Cl | OCF₃ | Cl |
| Cl | H | H | H | Cl | H | Cl | H | Cl | OH |
| Cl | H | Cl | H | H | Cl | H | H | H | Cl |
| Cl | H | Cl | H | H | Cl | H | Cl | H | H |
| Cl | H | Cl | H | H | Cl | H | CH₃ | H | H |
| Cl | H | Cl | H | H | CN | H | H | H | H |
| Cl | H | Cl | H | H | Br | H | H | H | Br |
| Cl | H | Cl | H | H | Br | H | Br | H | Br |
| Cl | H | Cl | H | H | Br | H | H | H | Cl |
| Cl | H | Cl | H | H | Cl | H | H | H | F |
| Cl | H | Cl | H | H | Cl | H | F | H | Cl |
| Cl | H | Cl | H | H | CF₃ | H | H | H | CF₃ |
| Cl | H | Cl | H | H | H | CF₃ | H | H | H |
| Cl | H | Cl | H | H | Cl | H | Cl | OCF₃ | Cl |
| Cl | H | Cl | H | H | H | Cl | H | Cl | OH |
| H | CF₃ | H | H | H | Cl | H | H | H | Cl |
| H | CF₃ | H | H | H | Cl | H | Cl | H | H |
| H | CF₃ | H | H | H | Cl | H | CH₃ | H | H |
| H | CF₃ | H | H | H | CN | H | H | H | H |
| H | CF₃ | H | H | H | Br | H | H | H | Br |
| H | CF₃ | H | H | H | Br | H | Br | H | Br |
| H | CF₃ | H | H | H | Br | H | H | H | Cl |
| H | CF₃ | H | H | H | Cl | H | H | H | F |
| H | CF₃ | H | H | H | Cl | H | F | H | Cl |
| H | CF₃ | H | H | H | CF₃ | H | H | H | CF₃ |
| H | CF₃ | H | H | H | H | CF₃ | H | H | H |
| H | CF₃ | H | H | H | Cl | H | Cl | OCF₃ | Cl |
| H | CF₃ | H | H | H | H | Cl | H | Cl | OH |
| Cl | H | H | H | F | Cl | H | H | H | Cl |
| Cl | H | H | H | F | Cl | H | Cl | H | H |
| Cl | H | H | H | F | Cl | H | CH₃ | H | H |
| Cl | H | H | H | F | CN | H | H | H | H |
| Cl | H | H | H | F | Br | H | H | H | Br |
| Cl | H | H | H | F | Br | H | Br | H | Br |
| Cl | H | H | H | F | Br | H | H | H | Cl |
| Cl | H | H | H | F | Cl | H | H | H | F |
| Cl | H | H | H | F | Cl | H | F | H | Cl |
| Cl | H | H | H | F | CF₃ | H | H | H | CF₃ |
| Cl | H | H | H | F | H | CF₃ | H | H | H |
| Cl | H | H | H | F | Cl | H | Cl | OCF₃ | Cl |
| Cl | H | H | H | F | H | Cl | H | Cl | OH |
| CF₃ | H | H | H | CF₃ | Cl | H | H | H | H |
| CF₃ | H | H | H | CF₃ | H | Cl | Cl | H | H |
| CF₃ | H | H | H | CF₃ | H | CF₃ | H | H | H |
| CF₃ | H | H | H | CF₃ | H | Cl | H | Cl | OH |

-continued

| X | R¹ | R²' | R³ | R⁴ | Y | R⁵ | R⁶ | R⁷ | R⁸ |
|---|---|---|---|---|---|---|---|---|---|
| CF₃ | H | H | H | CF₃ | Cl | H | Cl | H | H |
| CF₃ | H | H | H | CF₃ | Cl | H | H | H | Cl |
| Cl | H | Cl | OCF₃ | Cl | Cl | H | H | H | H |
| Cl | H | Cl | OCF₃ | Cl | Cl | H | H | H | Cl |
| Cl | H | Cl | OCF₃ | Cl | Cl | H | Cl | H | H |
| Cl | H | Cl | OCF₃ | Cl | H | Cl | Cl | H | H |
| Cl | H | Cl | OCF₃ | Cl | H | CF₃ | H | H | H |
| Cl | H | Cl | OCF₃ | Cl | H | OCH₃ | OH | Br | H |
| H | Cl | Cl | H | H | Cl | H | H | H | Cl |
| Cl | H | CH₃ | H | H | Cl | H | H | H | H |
| Cl | H | CH₃ | H | H | H | CF₃ | H | H | H |
| Cl | H | CH₃ | H | H | Cl | H | H | H | Cl |
| Cl | H | CH₃ | H | H | Cl | H | Cl | H | H |
| Cl | H | CH₃ | H | H | H | Cl | H | Cl | OH |
| Cl | H | CF₃ | H | Cl | Cl | H | Cl | H | H |
| Cl | H | CF₃ | H | Cl | H | CF₃ | H | H | H |
| Cl | H | CF₃ | H | Cl | Cl | H | H | H | Cl |
| Cl | H | CF₃ | H | Cl | H | Cl | H | Cl | OH |
| Cl | H | CF₃ | H | Cl | H | NO₂ | H | H | H |
| Cl | CF₃ | Cl | H | H | CH₃ | H | CH₃ | H | CH₃ |
| Cl | CF₃ | Cl | H | H | Cl | H | CH₃ | H | H |
| H | H | N(CH₃)₂ | H | H | Cl | H | H | H | Cl |

The new benzyl derivatives of 2,3-diaminomaleonitrile of the formula (I_C)

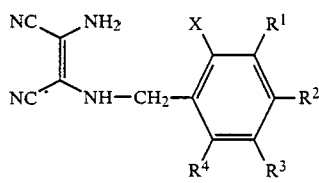

(I_C)

in which X, R¹, R², R³ and R⁴ possess the meanings given under formula (I), are obtained when azomethines of 2,3-diaminomaleonitrile of the formula (IV)

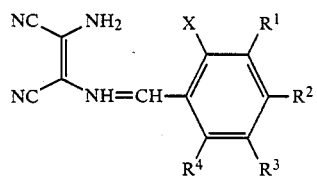

(IV)

in which
X, R¹, R², R³ and R⁴ have the abovementioned meanings, are reduced in a suitable solvent.

Finally, it has been found that the benzyl compounds of the formula (I_C) possess strongly pronounced acaricidal properties.

Surprisingly, the benzyl compounds of the formula (I_C) show an acaricidal activity. Such an action was hitherto unknown for the benzyl compounds of the diaminomaleonitrile class of substances. The compounds according to the invention therefore represent an enrichment of the prior art.

The compounds of the general formula (I_C) can exist in the stereoisomeric cis and/or trans forms, for example

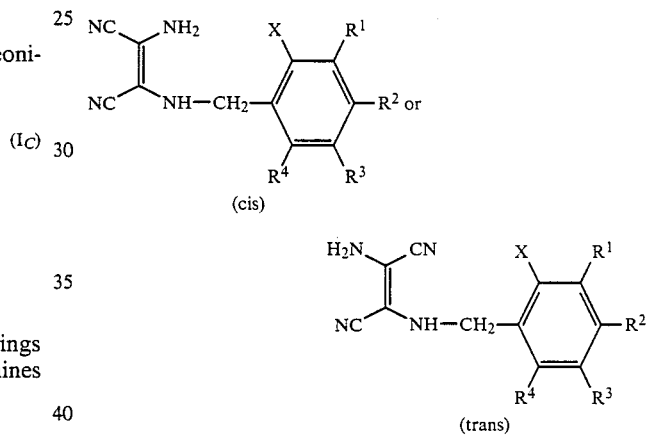

(cis)

(trans)

However, the compounds preferably exist in the cis form.

In the formula (I_C), X preferably represents fluorine, chlorine, bromine, iodine, CF₃ or CN.

In the radicals R¹, R², R³ and R⁴, suitable substituents for alkyl, alkoxy, dialkylamino, alkylthio, arylthio, alkylthionyl or alkylsulphonyl are preferably: halogen, in particular fluorine, chlorine and bromine and also OH and NH₂.

Preferred compounds are those of the formula (I_C) in which

W and R⁴ can be identical or different and represent fluorine, chlorine, bromine, iodine, CF₃ or CN, R¹, R² and R³ can be identical or different and represent hydrogen, alkyl(C₁-C₄), halogenoalkyl (C₁-C₄), alkoxy(C₁-C₄), halogenoalkoxy(C₁-C₄), halogen, CN, NO₂, dialkyl(C₁-C₄)amino, alkoxy(C₁-C₄)carbonyl, alkyl-(C₁-C₄)thio, alkyl(C₁-C₄)thionyl, dihalogenoalkyl-(C₁-C₄)amino, alkyl(C₁-C₄) sulphonyl, OH, SH or NH₂.

Particularly preferred compounds are those of the general formula (I_C')

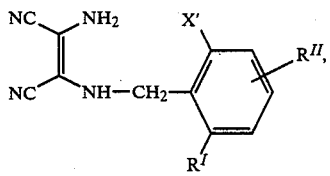

in which

X' and $R^I$ can be identical or different and represent fluorine, chlorine, bromine, iodine or $CF_3$ and $R^{II}$ represents hydrogen, chlorine, bromine, iodine, cyano, nitro, methyl, ethyl, n- and i-propyl, n-, i-, s- and t-butyl, methoxy, ethoxy, methoxycarbonyl, ethoxycarbonyl, trifluoromethyl, trichloromethyl, pentafluoroethyl, trifluoroethyl, trifluoromethylsulphone, trifluoromethoxy, trichloromethoxy, pentafluoroethoxy, dimethylamino, diethylamino, di-β-chloroethylamino or di-β-hydroxyethylamino.

Very particularly preferred compounds are those of the formula $(I_{C''})$

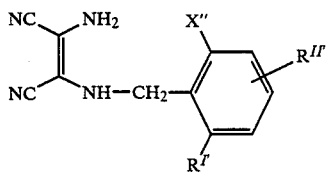

in which

X'' and $R^{I'}$ can be identical or different and represnt chlorine or bromine and $R^{II'}$ represents chlorine, bromine, iodine, hydrogen, cyano, nitro, methyl, ethyl, n- and i-propyl, methoxy, ethoxy, methoxycarbonyl, ethoxycarbonyl, trifluoromethyl, trichloromethyl, dimethylamino, diethylamino or trifluoromethylsulphone.

Compounds of very particular interest are those of the formula $(I_{C'''})$

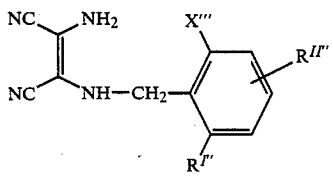

in which

X''' and $R^{I''}$ can be identical or different and represent chlorine or bromine, and $R^{II''}$ represents hydrogen, chlorine, bromine, methyl, cyano, trichloromethyl, trifluoromethyl, methoxy, trifluoromethoxy, trichloromethoxy or trifluoromethylsulphone.

Exceedingly preferred compounds are those of the general formula $(I_{C''''})$

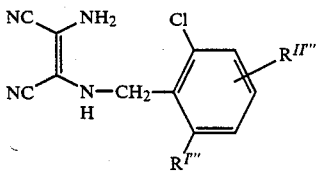

in which $R^{I'''}$ represents chlorine or bromine and $R^{II'''}$ represents hydrogen, chlorine, methyl, trichloromethyl, methoxy, trichloromethoxy or trifluoromethoxy.

An exceedingly preferred compound of the general formula $(I_C)$ according to the invention which may be mentioned is the compound of the formula

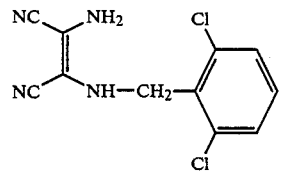

The azomethines of the formula (IV) required as starting materials for carrying out the process according to the invention can be obtained by the processes described in patent specification JP 51,151,325.

Suitable diluents for carrying out the process according to the invention are polar organic solvents such as, for example, alcohols (in particular methanol, ethanol, propanol (n and i)), dimethylformamide (DMF), dimethyl sulphoxide (DMSO), hexamethylphosphoric acid triamide (HMPT), as well as acetonitrile, diethyl ether and tetrahydrofuran.

The reaction temperature is generally in the range between about 0° C. up to a maximum of the boiling point of the particular solvent, in particular the reaction is carried out at temperatures of about 10° to about 50° C.

The reaction is preferably carried out at atmospheric pressure.

The reductants used are metal hydrides, for example of aluminium, tin and boron.

The use of sodium borohydride in protic solvents such as, for example, methanol, ethanol or in aprotic solvents such as, for example, DMF or hexamethylphosphoric acid triamide (HMPT) is preferred.

Working up is by customary methods, the product being filtered off with suction or extracted after discharging onto ice or water.

The preparation process for obtaining the compound of the formula $(I_C)$ can be presented as follows by means of an example:

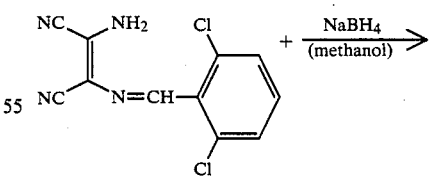

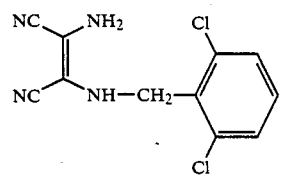

The following benzyl derivatives of 2,3-diaminomaleonitrile of the formula $(I_C)$

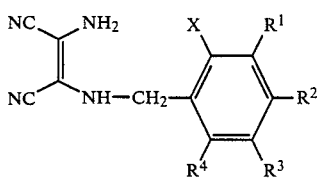

(I_C)

may be mentioned individually in addition to the compounds mentioned in the preparation examples:

| X | R¹ | R² | R³ | R⁴ |
|---|----|----|----|----|
| CF₃ | H | H | H | CF₃ |
| CN | H | H | H | H |
| Cl | H | H | H | H |
| H | Cl | H | H | H |
| H | H | Cl | H | H |
| Cl | H | F | H | Cl |
| Cl | H | Cl | H | Cl |
| Cl | H | Cl | Cl | H |
| Cl | H | H | H | SCH₃ |
| H | H | N(CH₃)₂ | H | H |
| H | Cl | H | Cl | OH |
| Cl | H | H | NO₂ | H |
| H | H | Br | H | H |
| F | F | F | F | F |
| H | H | F | Br | H |
| Cl | H | CF₃ | H | H |
| Cl | Cl | CF₃ | H | Cl |
| Cl | H | COOCH₃ | H | Cl |
| Cl | CF₃ | Cl | H | H |
| Br | H | Br | H | Br |
| Cl | H | Br | H | Cl |
| Cl | H | Cl | H | Br |
| Cl | H | CF₃ | H | Cl |
| Cl | H | OCF₃ | H | Cl |
| Cl | H | OCCl₃ | H | Cl |
| Cl | H | OCF₃ | H | H |
| Cl | H | OCCl₃ | H | H |
| Cl | H | OCH₃ | H | Cl |
| Cl | H | OCH₃ | H | H |
| Cl | H | SCF₃ | H | Cl |
| Cl | H | SO₂CF₃ | H | Cl |
| Cl | H | SCF₃ | H | H |
| Cl | H | SO₂CF₃ | H | H |
| Cl | H | CH₃ | H | H |
| Cl | H | H | H | CH₃ |
| Cl | H | CF₃ | H | CH₃ |
| Cl | H | OCF₃ | H | CH₃ |
| Cl | H | SO₂CF₃ | H | CH₃ |
| Cl | H | H | H | CN |
| Cl | H | CN | H | Cl |
| H | OCH₃ | OH | H | H |
| H | H | H | OCH₃ | OH |
| H | H | Cl | NO₂ | H |
| H | H | H | H | NO₂ |
| H | NO₂ | H | H | H |
| Br | H | H | H | Cl |
| H | H | NO₂ | H | H |
| H | Cl | CF₃ | H | H |
| H | Br | OH | OCH₃ | H |
| Br | H | H | H | Br |
| Br | H | CH₃ | H | H |
| CF₃ | H | F | H | CF₃ |
| Cl | H | H | Cl | H |
| Cl | H | Cl | OH | Cl |
| Cl | Cl | OH | Cl | H |
| F | F | OH | F | F |
| H | I | OH | I | H |
| Cl | H | H | H | SO₂CH₃ |
| Cl | H | H | H | SO₂CF₃ |
| H | H | CN | H | H |
| Br | H | CN | H | Br |
| Cl | H | CN | H | Cl |
| H | H | N(CH₂CH₂CN)₂ | H | H |
| H | H | N(CH₂CH₂Cl)₂ | H | H |

The new bisbenzyl derivatives of 2,3-diaminomaleonitrile of the formula (I_D)

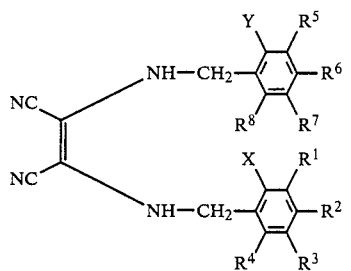

(I_D)

in which X, Y, R¹, R², R³, R⁴, R⁵, R⁶, R⁷ and R⁸ have the meanings given under formula (I_A), are obtained when the bisanils of the general formula (I_A)

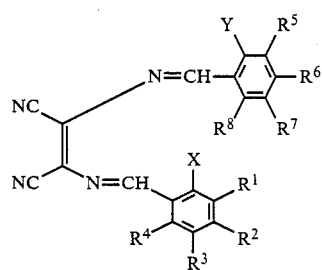

(I_A)

or the benzyl-benzylidene derivatives of the general formula (I_B)

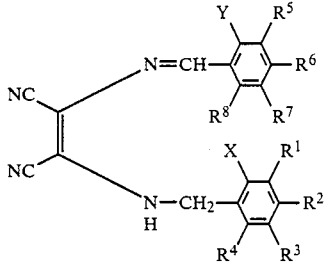

(I_B)

in which X, Y, R¹, R², R³, R⁴, R⁵, R⁶, R⁷ and R⁸ independently of one another have the abovementioned meanings are reduced in a suitable diluent.

The compounds of the general formula (I_D) can exist in the stereoisomeric cis and/or trans forms. However, the compounds preferably exist in the cis form.

Formula (I_D) provides a general definition of the acaricidally active bisbenzyl compounds.

In the formula (I_D), X and Y preferably represent hydrogen, fluorine, chlorine, bromine, iodine, CF₃ or CN.

In the radicals R¹, R², R³ and R⁴ and also R⁵, R⁶, R⁷ and R⁸, which can likewise be identical or different, suitable substituents for alkyl, alkoxy, dialkylamino, alkylthio, alkylthionyl or alkylsulphonyl are preferably: halogen, in particular fluorine, chlorine and bromine and also OH and NH₂.

Preferred compounds are those of the formula (I_D) in which

X and R⁴ and also Y and R⁸ can be identical or different and represent fluorine, chlorine, bromine, iodine, CF₃ or CN, R¹, R² and R³ and also R⁵, R⁶ and R⁷ can be identical or different and represent hydrogen, alkyl(-

$C_1$–$C_4$), halogenoalkyl($C_1$–$C_4$), alkoxy($C_1$–$C_4$), halogenoalkoxy ($C_1$–$C_4$), halogen, CN, $NO_2$, dialkyl($C_1$–$C_4$) amino, alkoxy($C_1$–$C_4$)carbonyl, alkyl($C_1$–$C_4$)thio, alkyl($C_1$–$C_4$)thionyl, dihalogenoalkyl($C_1$–$C_4$)amino, alkyl($C_1$–$C_4$)sulphonyl, OH, SH or $NH_2$. Particularly preferred compounds are those of the general formula ($I_{D'}$)

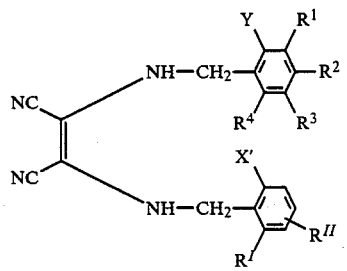

in which

X, $R^1$, $R^2$, $R^3$ and $R^4$ have the abovementioned meanings and $X'$ and $R^I$ can be identical or different and represent fluorine, chlorine, bromine, iodine or $CF_3$ and $R^{II}$ represents hydrogen, chlorine, bromine, iodine, cyano, nitro, methyl, ethyl, n- and i-propyl, n-, i-, s- and t-butyl, methoxy, ethoxy, methoxycarbonyl, ethoxycarbonyl, trifluoromethyl, trichloromethyl, pentafluoroethyl, trifluoroethyl, trifluoromethylsulphone, trifluoromethoxy, trichloromethoxy, pentafluoroethoxy, dimethylamino, diethylamino, di-$\beta$-chloroethylamino or di-$\beta$-hydroxyethylamino.

Very particularly preferred compounds are those of the formula ($I_{D''}$)

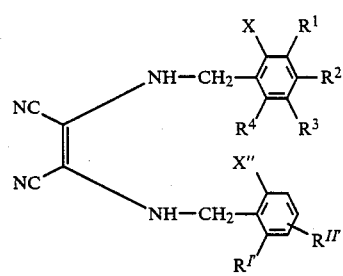

in which $X''$ and $R^I$ can be identical or different and represent chlorine or bromine and $R^{II}$ represents chlorine, bromine, iodine, hydrogen, cyano, nitro, methyl, ethyl, n- and i-propyl, methoxy, ethoxy, methoxycarbonyl, ethoxycarbonyl, trifluoromethyl, trichloromethyl, dimethylamino, diethylamino or trifluoromethylsuphone.

Exceeding preferred compounds are those of the formula ($I_{D'''}$)

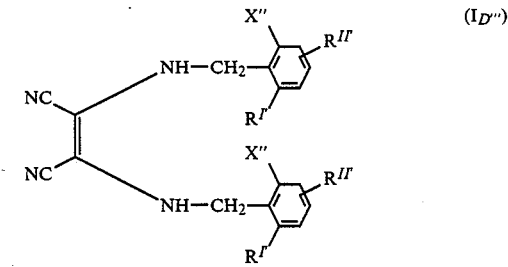

in which $X'''$ and $R^I$ can be identical or different and represent chlorine or bromine and $R^{II}$ represents chlorine, bromine, iodine, hydrogen, cyano, nitro, methyl, ethyl, n- and i-propyl, methoxy, ethoxy, methoxycarbonyl, ethoxycarbonyl, trifluoromethyl, trichloromethyl, dimethylamino, diethylamino or trifluoromethylsulphone.

Compounds of very particular interest are furthermore those of the formula ($I_{D''''}$)

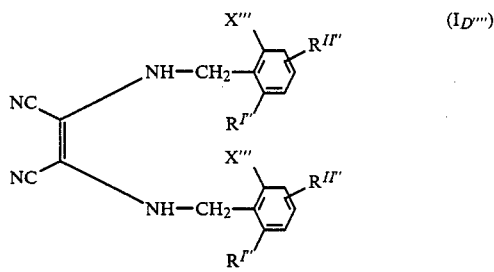

in which $X''''$ and $R^{I'}$ represent chlorine or bromine and $R^{II'}$ represents hydrogen, chlorine, methyl, trifluoromethyl, methoxy, trichloromethyl, ethoxy, trichloromethoxy or trifluoromethoxy.

Suitable diluents for crrying out the process according to the invention are polar organic solvents such as, for example, alcohols (in particular methanol, ethanol, propanol (n and i)) dimethylformamide (DMF), dimethyl sulphoxide (DMSO), hexamethylphosphoric acid triamide (HMPT), and also acetonitrile, diethyl ether and tetrahydrofuran.

The reaction temperature is in general in the range between about 0° C. up to a maximum of the boiling point of the particular solvent, in particular the reaction is carried out at temperatures of about 10° to about 50° C.

The reaction is preferably carried out at atmospheric pressure.

The reductants used are preferably metal hydrides, for example, hydrides of aluminium, tin and boron.

Sodium borohydride in protic solvents such as, for example, methanol, ethanol or in aprotic solvents such as, for example, DMF, tetrahydrofuran or hexamethylphosphoric acid triamide (HMPT) is preferred.

Working up is by customary methods, the product generally being filtered off with suction or extracted after discharging onto ice or water.

The preparation process for obtaining the compounds ($I_D$) can be represented by means of an example as follows:

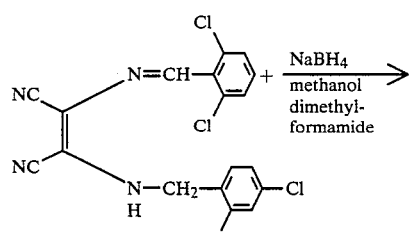

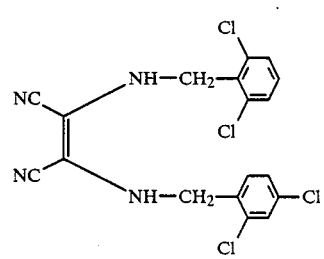

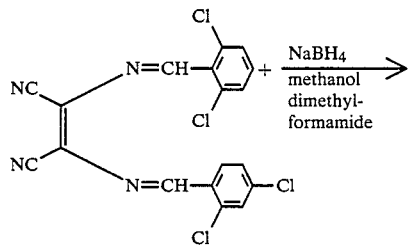

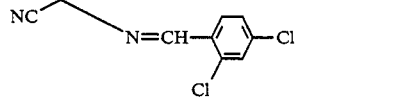

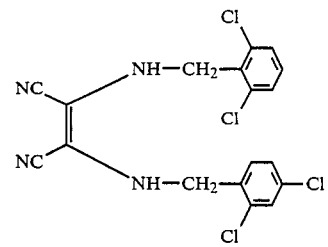

The following bisbenzyl compounds of 2,3-diaminomaleonitrile of the formula ($I_D$)

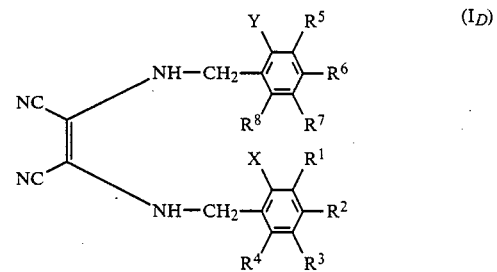

may be mentioned individually in addition to the compounds mentioned in the preparation examples:

| X | R¹ | R² | R³ | R⁴ | Y | R⁵ | R⁶ | R⁷ | R⁸ |
|---|----|----|----|----|----|-----|-----|-----|-----|
| H | H | H | H | H | Cl | H | H | H | H |
| H | H | H | H | H | Cl | H | Cl | H | H |
| H | H | H | H | H | Cl | H | Cl | H | Cl |
| H | H | H | H | H | Cl | H | H | H | F |
| H | H | H | H | H | H | CF₃ | H | H | H |
| H | H | H | H | H | CF₃ | H | H | H | CF₃ |
| H | H | H | H | H | Cl | OCF₃ | Cl | H | Cl |
| H | H | H | H | H | F | F | F | F | F |
| H | H | H | H | H | F | F | OH | F | F |
| H | H | H | H | H | CF₃ | H | F | H | CF₃ |
| H | H | H | H | H | Cl | H | F | H | Cl |
| H | H | H | H | H | Br | H | H | H | Cl |
| H | H | H | H | H | Cl | H | CF₃ | H | H |
| H | H | H | H | H | Cl | Cl | CF₃ | H | Cl |
| H | H | H | H | H | Cl | H | COOCH₃ | H | Cl |
| H | H | H | H | H | Cl | H | OCH₃ | H | Cl |
| H | H | H | H | H | Cl | H | SCF₃ | H | Cl |
| H | H | H | H | H | Cl | H | SO₂CF₃ | H | Cl |
| H | H | H | H | H | Cl | H | CH₃ | H | H |
| H | H | H | H | H | Br | H | H | H | F |
| H | H | H | H | H | H | OCH₃ | H | H | H |
| H | H | H | H | H | H | H | Cl | NO₂ | H |
| H | H | H | H | H | CN | H | H | H | Cl |
| H | H | H | H | H | H | H | CN | H | H |
| H | H | H | H | H | H | Br | OH | OCH₃ | H |
| Cl | H | H | H | H | Cl | H | H | H | Cl |
| Cl | H | H | H | H | Cl | H | Cl | H | H |
| Cl | H | H | H | H | Cl | H | CH₃ | H | H |
| Cl | H | H | H | H | CN | H | H | H | H |
| Cl | H | H | H | H | Br | H | Br | H | Br |
| Cl | H | H | H | H | Br | H | H | H | Cl |
| Cl | H | H | H | H | Cl | H | F | H | Cl |
| Cl | H | H | H | H | CF₃ | H | H | H | CF₃ |
| Cl | H | H | H | H | H | CF₃ | H | H | H |
| Cl | H | H | H | H | CF₃ | H | F | H | CF₃ |
| Cl | H | H | H | H | Cl | H | H | H | F |
| Cl | H | H | H | H | Cl | OCF₃ | Cl | H | Cl |
| Cl | H | H | H | H | H | Cl | H | Cl | OH |
| H | Cl | H | H | H | Cl | H | H | H | Cl |
| H | Cl | H | H | H | Cl | H | Cl | H | H |
| H | Cl | H | H | H | Cl | H | CH₃ | H | H |
| H | Cl | H | H | H | CN | H | H | H | H |

-continued

| X | R¹ | R² | R³ | R⁴ | Y | R⁵ | R⁶ | R⁷ | R⁸ |
|---|----|----|----|----|---|----|----|----|----|
| H | Cl | H | H | H | Br | H | H | H | Br |
| H | Cl | H | H | H | Br | H | Br | H | Br |
| H | Cl | H | H | H | Br | H | H | H | Cl |
| H | Cl | H | H | H | Cl | H | H | H | F |
| H | Cl | H | H | H | Cl | H | F | H | Cl |
| H | Cl | H | H | H | CF₃ | H | H | H | CF₃ |
| H | Cl | H | H | H | H | CF₃ | H | H | H |
| H | Cl | H | H | H | Cl | H | Cl | OCF₃ | Cl |
| H | Cl | H | H | H | H | Cl | H | Cl | OH |
| H | H | Cl | H | H | Cl | H | H | H | Cl |
| H | H | Cl | H | H | Cl | H | Cl | H | H |
| H | H | Cl | H | H | Cl | H | Cl | H | Cl |
| H | H | Cl | H | H | Cl | H | CH₃ | H | H |
| H | H | Cl | H | H | CN | H | H | H | H |
| H | H | Cl | H | H | Br | H | H | H | Br |
| H | H | Cl | H | H | Br | H | Br | H | Br |
| H | H | Cl | H | H | Br | H | H | H | Cl |
| H | H | Cl | H | H | Cl | H | H | H | F |
| H | H | Cl | H | H | Cl | H | F | H | Cl |
| H | H | Cl | H | H | CF₃ | H | H | H | CF₃ |
| H | H | Cl | H | H | H | CF₃ | H | H | H |
| H | H | Cl | H | H | Cl | H | Cl | OCF₃ | Cl |
| H | H | Cl | H | H | H | Cl | H | Cl | OH |
| Cl | H | H | H | Cl | Cl | H | H | H | Cl |
| Cl | H | H | H | Cl | Cl | H | Cl | H | H |
| Cl | H | H | H | Cl | Cl | H | CH₃ | H | H |
| Cl | H | H | H | Cl | CN | H | H | H | H |
| Cl | H | H | H | Cl | Br | H | H | H | H |
| Cl | H | H | H | Cl | Br | H | Br | H | Br |
| Cl | H | H | H | Cl | Br | H | H | H | Cl |
| Cl | H | H | H | Cl | Cl | H | H | H | F |
| Cl | H | H | H | Cl | H | H | H | H | Cl |
| Cl | H | H | H | Cl | Br | H | H | H | Br |
| Cl | H | H | H | Cl | H | H | H | H | CH₃ |
| Cl | H | H | H | Cl | Cl | H | F | H | Cl |
| Cl | H | H | H | Cl | CF₃ | H | H | H | CF₃ |
| Cl | H | H | H | Cl | H | CF₃ | H | H | H |
| Cl | H | H | H | Cl | Cl | H | Cl | OCF₃ | Cl |
| Cl | H | H | H | Cl | H | Cl | H | Cl | OH |
| Cl | H | Cl | H | H | Cl | H | H | H | Cl |
| Cl | H | Cl | H | H | Cl | H | Cl | H | H |
| Cl | H | Cl | H | H | Cl | H | CH₃ | H | H |
| Cl | H | Cl | H | H | CN | H | H | H | H |
| Cl | H | Cl | H | H | Br | H | H | H | Br |
| Cl | H | Cl | H | H | Br | H | Br | H | Br |
| Cl | H | Cl | H | H | Br | H | H | H | Cl |
| Cl | H | Cl | H | H | Cl | H | H | H | F |
| Cl | H | Cl | H | H | Cl | H | F | H | Cl |
| Cl | H | Cl | H | H | CF₃ | H | H | H | CF₃ |
| Cl | H | Cl | H | H | H | CF₃ | H | H | H |
| Cl | H | Cl | H | H | Cl | H | Cl | OCF₃ | Cl |
| Cl | H | Cl | H | H | H | Cl | H | Cl | OH |
| H | CF₃ | H | H | H | Cl | H | H | H | Cl |
| H | CF₃ | H | H | H | Cl | H | Cl | H | H |
| H | CF₃ | H | H | H | Cl | H | CF₃ | H | H |
| H | CF₃ | H | H | H | CN | H | H | H | H |
| H | CF₃ | H | H | H | Br | H | H | H | Br |
| H | CF₃ | H | H | H | Br | H | Br | H | Br |
| H | CF₃ | H | H | H | Br | H | H | H | Cl |
| H | CF₃ | H | H | H | Cl | H | H | H | F |
| H | CF₃ | H | H | H | Cl | H | F | H | Cl |
| H | CF₃ | H | H | H | CF₃ | H | H | H | CF₃ |
| H | CF₃ | H | H | H | H | CF₃ | H | H | H |
| H | CF₃ | H | H | H | Cl | H | Cl | OCF₃ | Cl |
| H | CF₃ | H | H | H | H | Cl | H | Cl | OH |
| Cl | H | H | H | F | Cl | H | H | H | Cl |
| Cl | H | H | H | F | Cl | H | Cl | H | H |
| Cl | H | H | H | F | Cl | H | CH₃ | H | H |
| Cl | H | H | H | F | CN | H | H | H | H |
| Cl | H | H | H | F | Br | H | H | H | Br |
| Cl | H | H | H | F | Br | H | Br | H | Br |
| Cl | H | H | H | F | Br | H | H | H | Cl |
| Cl | H | H | H | F | Cl | H | H | H | F |
| Cl | H | H | H | F | Cl | H | F | H | Cl |
| Cl | H | H | H | F | CF₃ | H | H | H | CF₃ |
| Cl | H | H | H | F | H | CF₃ | H | H | H |
| Cl | H | H | H | F | Cl | H | Cl | OCF₃ | Cl |
| Cl | H | H | H | F | H | Cl | H | Cl | OH |
| CF₃ | H | H | H | CF₃ | Cl | H | H | H | H |
| CF₃ | H | H | H | CF₃ | H | Cl | Cl | H | H |
| CF₃ | H | H | H | CF₃ | H | CF₃ | H | H | H |

-continued

| X | R¹ | R² | R³ | R⁴ | Y | R⁵ | R⁶ | R⁷ | R⁸ |
|---|---|---|---|---|---|---|---|---|---|
| CF₃ | H | H | H | CF₃ | H | Cl | H | Cl | OH |
| CF₃ | H | H | H | CF₃ | Cl | H | Cl | H | H |
| CF₃ | H | H | H | CF₃ | Cl | H | H | H | Cl |
| Cl | H | Cl | OCF₃ | Cl | Cl | H | H | H | H |
| Cl | H | Cl | OCF₃ | Cl | Cl | H | H | H | Cl |
| Cl | H | Cl | OCF₃ | Cl | Cl | H | Cl | H | H |
| Cl | H | Cl | OCF₃ | Cl | H | Cl | Cl | H | H |
| Cl | H | Cl | OCF₃ | Cl | H | CF₃ | H | H | H |
| Cl | H | Cl | OCF₃ | Cl | H | OCH₃ | OH | Br | H |
| H | Cl | Cl | H | H | Cl | H | H | H | Cl |
| Cl | H | CH₃ | H | H | Cl | H | H | H | H |
| Cl | H | CH₃ | H | H | H | CF₃ | H | H | H |
| Cl | H | CH₃ | H | H | Cl | H | H | H | Cl |
| Cl | H | CF₃ | H | H | Cl | H | Cl | H | H |
| Cl | H | CH₃ | H | H | H | Cl | H | Cl | OH |
| Cl | H | CF₃ | H | Cl | Cl | H | Cl | H | H |
| Cl | H | CF₃ | H | Cl | H | CF₃ | H | H | H |
| Cl | H | CF₃ | H | Cl | Cl | H | H | H | Cl |
| Cl | H | CF₃ | H | Cl | H | Cl | H | Cl | OH |
| Cl | H | CF₃ | H | Cl | H | NO₂ | H | H | H |
| Cl | CF₃ | Cl | H | H | CF₃ | H | CH₃ | H | CH₃ |
| Cl | CF₃ | Cl | H | H | Cl | H | CH₃ | H | H |
| H | H | N(CH₃)₂ | H | H | Cl | H | H | H | Cl |

The active compounds are suitable for combating animal pests, in particular of the class of arachnida and the order of mites (Acarina), which are encountered in agriculture, in forestry, in the protection of stored products and of materials, and in the hygiene field, and have good plant tolerance and favourable toxicity to warm-blooded animals. They are active against normally sensitive and resistant species and against all or some stages of development. The abovementioned pests include:

From the order of the Acarina, for example, *Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp.* and *Tetranychus spp.*

The active compounds according to the invention are not only active against plant, hygiene and stored product pests, but also, in the veterinary medicine sector, against animal parasites (ectoparasites), such as scaly ticks, argasidae, scab mites and trombidae. They are active against normally sensitive and resistant species and strains, as well as against all parasitic and non-parasitic stages of development of the ectoparasites.

The active compounds according to the invention are distinguished by a high acaricidal activity. They can be employed particularly successfully against mites which are harmful to plants, such as, for example, against the common spider mite (*Tetranychus urticae*).

Moreover, the compounds according to the invention also exhibit a fungicidal activity.

The active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, and furthermore into formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is emulsifying agents and-/or dispersing agents, and/or foam-forming agents. In the case of the use of water as an extender, organic solvents can, for example, also be used as auxiliary solvent. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example, mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example, aerosol propellant, such as halogenated hydrocarbons as well as butane, propane, nitrogen and carbon dioxide; as solid carriers there are suitable: for example, ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example, non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysation products; as dispersing agents there are suitable: for example, ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example, iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides or fungicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

The active compounds which can be used according to the invention are also suitable for combating mites, ticks etc. in the sector of animal husbandry and cattle breeding; better results, for example higher milk production, greater weight, more attractive animal pelt, longer life etc., can be achieved by combating the pests.

The application of the active compounds which can be used according to the invention occurs in this sector in a known fashion, such as by oral application in the form of, for example, tablets, capsules, potions, granules, by means of dermal or external application in the form of, for example, dipping, spraying, pouring-on, spotting-on and dusting, as well as by means of parenteral application in the form, for example, of injection, and, furthermore, by means of the feed-through process. In addition, application as molded articles (collar, ear tag) is also possible.

Examples

Example A

Tetranychus test (resistant)
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with the common spider mite or two-spotted spider mite (*Tetranychus urticae*) in all stages of development are treated by being dipped into the preparation of the active compound of the desired concentration.

After the desired period of time, the destruction in % is determined. 100% means that all the spider mites have been killed; 0% means that none of the spider mites have been killed.

In this test, for example, the following compounds from the preparation examples show strong activity against spider mites: (3), (9), (12), (14), (15) and (26).

Table A

| Active compounds (plant-damaging mites) | Compound of active compound in % | Degree of destruction in % after 7 days |
|---|---|---|
| (3) | 0.1 | 98 |
| (26) | 0.1 | 98 |
| (9) | 0.1 | 98 |
| (14) | 0.1 | 98 |
| (15) | 0.1 | 98 |

Table A-continued
(plant-damaging mites)

| Active compounds | Compound of active compound in % | Degree of destruction in % after 7 days |
|---|---|---|
| 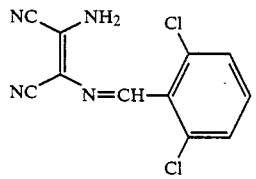 (12) | 0.1 | 98 |

PREPARATION EXAMPLES

EXAMPLE 1

13.25 g of N-2,6-dichlorobenzylidene-amino-maleonitrile are heated to reflux in 100 ml of absolute ethanol with 5.3 g of benzaldehyde and 100 mg of p-toluenesulphonic acid. The mixture is allowed to boil for a further 4 hours and then discharged onto 500 g of ice. 13.0 g of the following compound of melting point >250° C. (dec.) are isolated by filtering off with suction:

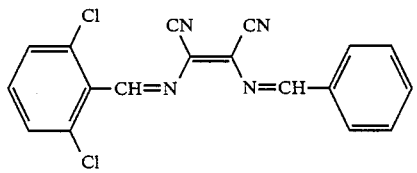

EXAMPLE 2

If 3-trifluoromethylbenzaldehyde is used instead of benzaldehyde in the above example and the same reaction conditions are otherwise employed, then the following compound of melting point 243° C. is obtained.

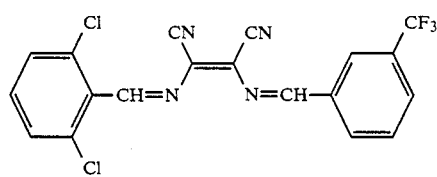

EXAMPLE 1A

The starting compound N-2,6-dichlorobenzylideneamino-maleonitrile of the formula employed in Examples 1 and 2 can be prepared as follows:

A mixture of 10.8 g of 2,3-diaminomaleonitrile and 17.5 g of 2,6-dichlorobenzaldehyde are brought to boiling in 100 ml of acetonitrile. Thin-layer chromatography indicates completion of the reaction after 4 hours. After cooling, 24.2 g (91% of theory) of N-2,6-dichlorobenzylideneaminomaleonitrile are filtered off with suction. The substance (yellow-green needles) melts at 191° C.

EXAMPLE 3

A mixture of 10.8 g of 2,3-diaminomaleonitrile and 17.5 g of 2,6-dichlorobenzaldehyde is brought to boiling in 200 ml of methanol. Thin-layer chromatography indicates the formation of the azomethine after 4 hours. The reaction batch is then cooled to 0° C. and 4.0 g of sodium borohydride are added in portions. The mixture is stirred for a further 30 minutes until a clear brown solution is obtained. After thin-layer chromatographic checking, the batch is discharged onto 500 g of ice and the precipitated product is filtered off with suction. 22.8 g of the following compound.

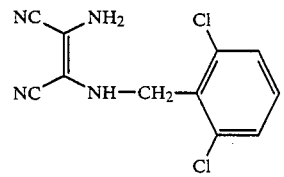

are obtained in the form of a yellow-brown powder of melting point 159° C. (from toluene).

EXAMPLE 4

1.8 g of sodium borohydride is added to a solution of 11.88 g of 3-trifluoromethylbenzylidenediaminomaleonitrile in 100 ml of methanol at 0° to 5° C. Thin-layer chromatography indicates completion of the reaction. The reaction batch is discharged onto 500 g of ice and the product is filtered off with suction. 9.2 g of a product of the following formula are obtained which melts at 79° C. after recrystallization from a little chloroform.

The following compounds are obtained analogously to the abovementioned examples.

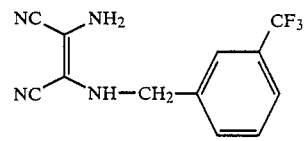

| Example No. | $R_A^1$ | $R_A^2$ | $R_A^3$ | $R_A^4$ | $R_A^5$ | Melting point |
|---|---|---|---|---|---|---|
| 5 | Cl | H | Cl | OCF$_3$ | Cl | 158°C. |
| 6 | Cl | H | H | H | F | 141° C. |
| 7 | H | H | H | H | H | 112° C. |
| 8 | Cl | H | Cl | H | H | 122° C. |

EXAMPLE 9

8.75 g of 2,6-dichlorobenzaldehyde are added to 13.35 g of N-2,6-dichlorobenzyl-amino-maleonitrile, prepared according to Example 3, in 100 ml of acetonitrile and the mixture is heated to reflux. The azomethine crystallizes even while still hot. The mixture is allowed to cool and the yellow crystals filtered off with suction. 39.2 g of the following compound of melting point 132° C. are obtained.

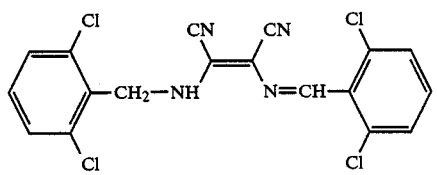

EXAMPLE 10

5.01 g of N-2-fluoro-6-chloro-benzyl-amino-maleonitrile prepared according to Example 6 are heated at reflux with 3.5 g of 2,6-dichlorobenzaldehyde in 50 ml of acetonitrile. After 4 hours, the mixture is cooled considerably and 6.7 g of the following compound are filtered off with suction.

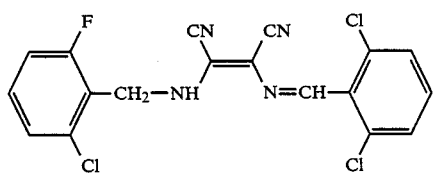

It melts at 159° to 163° C.

The following compounds are obtained analogously to Examples 9 and 10 above.

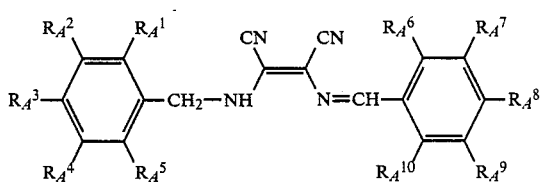

| Example No. | $R_A{}^1$ | $R_A{}^2$ | $R_A{}^3$ | $R_A{}^4$ | $R_A{}^5$ | $R_A{}^6$ | $R_A{}^7$ | $R_A{}^8$ | $R_A{}^9$ | $R_A{}^{10}$ | Melting point |
|---|---|---|---|---|---|---|---|---|---|---|---|
| 11 | Cl | H | H | H | Cl | H | $CF_3$ | H | H | H | 151° C. |
| 12 | H | H | H | H | H | Cl | H | H | H | Cl | 126° C. |
| 13 | H | H | H | H | H | H | H | $N(CH_3)_2$ | H | H | 195° C. |
| 14 | Cl | H | Cl | H | Cl | H | Cl | H | H | Cl | 194° C. |
| 15 | Cl | H | H | H | Cl | Cl | H | Cl | H | H | 152° C. |
| 16 | H | Cl | H | H | H | OH | Cl | H | Cl | H | 217° C. |
| 17 | Cl | H | H | H | Cl | H | Cl | $OCF_3$ | Cl | H | 128° C. |
| 18 | H | Cl | H | H | H | H | Cl | Cl | H | H | 201° C. |
| 19 | H | Cl | H | H | H | Cl | H | Cl | H | H | 193° C. |
| 20 | H | H | H | H | H | Cl | H | H | H | Cl | 139° C. |
| 21 | Cl | H | H | H | H | H | Cl | Cl | H | H | 174° C. |
| 22 | Cl | H | H | H | Cl | H | Cl | H | H | H | 183° C. |
| 23 | Cl | H | H | H | H | Cl | H | H | H | Cl | 164° C. |
| 24 | Cl | H | H | H | Cl | H | Cl | Cl | H | H | 202° C. |

EXAMPLE 25

21.2 g of N-2,4-dichlorobenzyl-N-2,6-dichlorobenzylidene-maleonitrile prepared according to Example 14 are dissolved in 100 ml of dimethylformamide and 300 ml of methanol, and 2.0 g of sodium borohydride are added at 0° C. The solution is then stirred for a further 1 hour at 25° C. The reaction conversion is monitored by thin-layer chromatography. Working up is carried out by discharging onto 500 g of ice and filtering off the precipitate with suction. 20.5 g of the following compound of melting point 101° C. are obtained (from isopropanol).

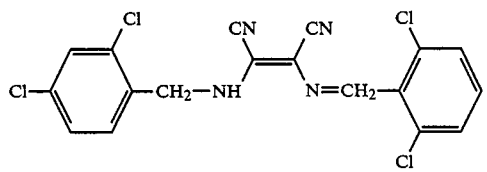

EXAMPLE 26

The following compound of melting point 124° C. is obtained (from isopropanol) according to the process described above from N-2,6-dichlorobenzyl-N-2,6-dichlorobenzylidene-maleonitrile obtainable according to Example 9 by reduction with sodium borohydride:

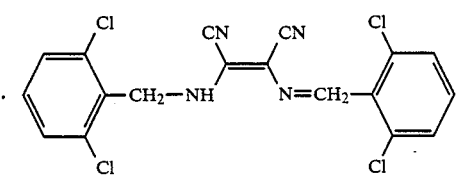

FORMULATION EXAMPLES

1. Dusting agents

For the preparation of a suitable active compound preparation, 5 parts by weight of active compound according to Example 9 are mixed with 95 parts by weight of ground natural minerals and ground to a powder. The agent thus obtained is applied by dusting to the plants or their environment in the amount desired in each case.

2. Wettable powder (dispersible powder)

For the production of a suitable active compound preparation, 50 parts by weight of active compound according to Example 3 are mixed with 1 part by weight of dibutylnaphthalenesulphonate, 4 parts by weight of ligninsulphonate, 8 parts by weight of highly disperse silica and 37 parts by weight of ground natural minerals, and the mixture is ground to a powder. Before application, the wettable powder is stirred with sufficient water so that the resultant mixture contains the active compound in the desired concentration in each case.

3. Emulsifiable concentrate

For the preparation of a suitable active compound preparation, 25 parts by weight of active compound according to Example 14 are dissolved in a mixture of 55 parts by weight of xylene and 10 parts by weight of cyclohexanone. 10 parts by weight of a mixture of calcium dodecylbenzenesulphonate and nonylphenol polyglycol ether are then added as emulsifier. Before application, the emulsion concentrate is diluted with sufficient water so that the resultant mixture contains the active compound in the desired concentration in each case.

4. Granules

For the preparation of a suitable active compound preparation, 2 parts by weight of a spindle oil and then 7 parts by weight of a finely ground mixture of active compound, which in turn contains 75 parts by weight of active compound according to Example 12 and 25 parts by weight of ground natural minerals, are added to 91 parts by weight of sand of a grain size 0.5 to 1.0 mm. The mixture is treated in a suitable mixer until uniform, free-flowing granules which do not form a dust result. The granules are scattered onto the plants or their environment in the amount desired in each case.

It will be appreciated that the instant specification and claims are set forth by way of illustration and not limitation, and that various modifications and changes may be made without departing from the spirit and scope of the present invention.

What is claimed is:

1. A method for combating arachnida which comprises applying to arachnida and/or to a habitat thereof an effective arachnida pest combating amount of at least one derivative of a 2,3-diaminomaleonitrile of the formula

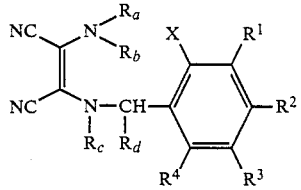 (I)

in which
X represents hydrogen, halogen, halogenoalkyl or CN,
$R^1$, $R^2$, $R^3$ and $R^4$ are identical or different and represent hydrogen, unsubstituted or substituted $C_1$-$C_4$ alkyl, unsubstituted or substituted $C_1$-$C_4$ alkoxy, halogen, CN, $NO_2$, unsubstituted or substituted di-alkylamino having up to 4 carbon atoms, alkoxy($C_1$-$C_4$)carbonyl, unsubstituted or substituted alkyl($C_1$-$C_4$) thio, unsubstituted or substituted alkyl($C_1$-$C_4$)thionyl, unsubstituted or substituted alkyl($C_1$-$C_4$)sulphonyl, OH, SH or $NH_2$,
wherein $R_a$ and $R_b$ together represent the radical

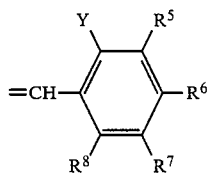

in which
Y represents hydrogen, halogen, halogenalkyl or CN,
$R^5$, $R^6$, $R^7$ and $R^8$ are identical or different and represent hydrogen, unsubstituted or substituted ($C_1$-$C_4$) alkyl, unsubstituted or substituted ($C_1$-$C_4$) alkoxy, halogen, CN, $NO_2$, unsubstituted or substituted dialkylamino having up to 4 carbon atoms, alkoxy($C_1$-$C_4$)carbonyl, unsubstituted or substituted alkyl($C_1$-$C_4$)thio, unsubstituted or substituted alkyl($C_1$-$C_4$)thionyl, unsubstituted or substituted alkyl($C_1$-$C_4$)sulphonyl, OH, SH or $NH_2$, and in which $R_c$ and $R_d$ together represent a chemical bond,
or $R_a$ and $R_b$ together represent the radical

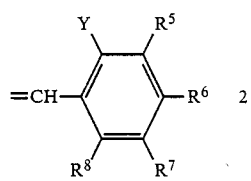 2 in which Y, $R^5$, $R^6$, $R^7$ and $R^8$ possess the meanings given above and in which $R_c$ and $R_d$ in each case represent hydrogen,
or $R_a$, $R_b$, $R_c$ and $R_d$ in each case represent hydrogen,
or $R_a$ represents hydrogen and $R_b$ represents the radical

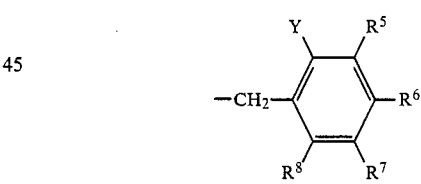

in which Y, $R^5$, $R^6$, $R^7$ and $R^8$ possess the meanings given above and $R_c$ and $R_d$ represent hydrogen, wherein the substituents for the alkyl, alkoxy, dialkylamino, alkylthio, alkylthionyl and alkylsulphonyl are selected from the group consisting of halogen, OH and $NH_2$.

2. A method according to claim 1, wherein the 2,3-diaminomaleonitrile is selected from the group consisting of

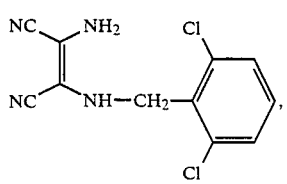

-continued
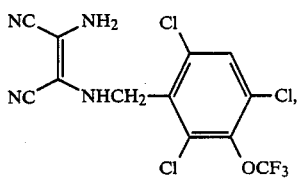
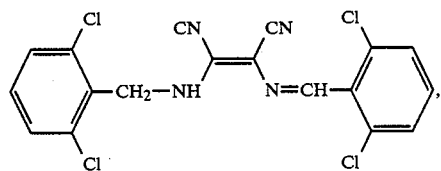
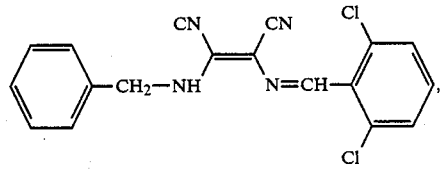
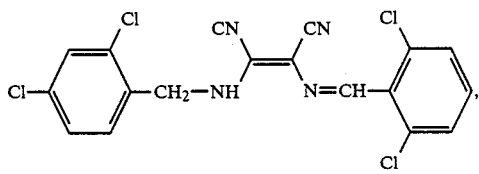
-continued
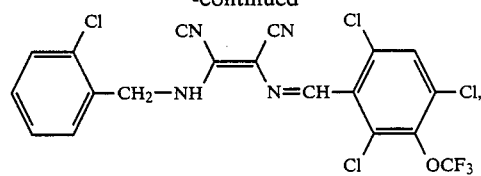
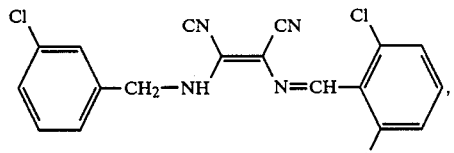
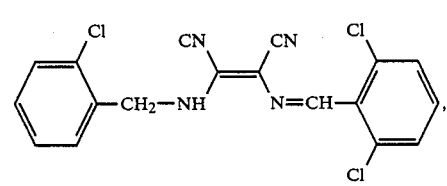
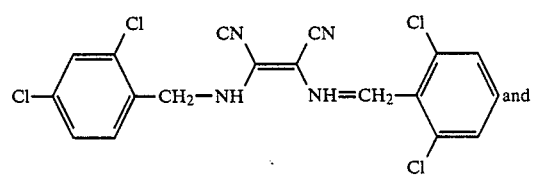
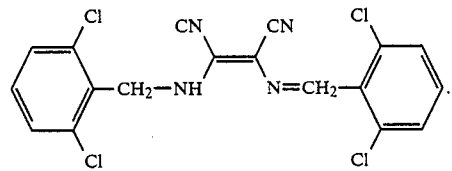
3. A method according to claim 1, wherein X is a halogen selected from the group consisting of fluorine, chlorine, bromide and iodine.
4. A method according to claim 1, wherein Y is a halogen selected from the group consisting of fluorine, chlorine, bromine and iodine.
* * * * *

UNITED STATES PATENT AND TRADEMARK OFFICE
CERTIFICATE OF CORRECTION

PATENT NO. : 4,897,419

DATED : January 30, 1990

INVENTOR(S) : Heidenreich et al.

It is certified that error appears in the above-identified patent and that said Letters Patent is hereby corrected as shown below:

Title Page     ABSTRACT: line 11 after " wherein " delete " $R_1$ " and substitute -- $R_a$ --

Col. 44, claim 1, line 30     To the right of the ring delete " 2 "

Col. 46, claim 2, line 34     Last group delete " $N=CH_2-$ " and substitute -- $NH-CH_2-$ --

Signed and Sealed this

Fifth Day of November, 1991

Attest:

HARRY F. MANBECK, JR.

*Attesting Officer*     *Commissioner of Patents and Trademarks*